United States Patent
Gordon et al.

(10) Patent No.: US 10,717,773 B2
(45) Date of Patent: Jul. 21, 2020

(54) POLYPEPTIDE TAGGING FUSIONS AND METHODS

(71) Applicant: REGENTS OF THE UNIVERSITY OF MINNESOTA, Minneapolis, MN (US)

(72) Inventors: Wendy Ryan Gordon, Saint Paul, MN (US); Klaus Norman Lovendahl, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 181 days.

(21) Appl. No.: 15/159,381

(22) Filed: May 19, 2016

(65) Prior Publication Data
US 2016/0340395 A1 Nov. 24, 2016

Related U.S. Application Data

(60) Provisional application No. 62/163,506, filed on May 19, 2015.

(51) Int. Cl.
*C07K 14/47* (2006.01)
*C12N 9/22* (2006.01)
*G01N 33/53* (2006.01)

(52) U.S. Cl.
CPC ............ *C07K 14/4702* (2013.01); *C12N 9/22* (2013.01); *G01N 33/5308* (2013.01); *C07K 2319/61* (2013.01); *C07K 2319/80* (2013.01); *C07K 2319/85* (2013.01); *C12Y 301/00* (2013.01); *G01N 33/53* (2013.01)

(58) Field of Classification Search
CPC combination set(s) only.
See application file for complete search history.

(56) References Cited

U.S. PATENT DOCUMENTS

| | | | |
|---|---|---|---|
| 5,643,758 A | 7/1997 | Guan | |
| 2005/0272114 A1 | 12/2005 | Darzins | |
| 2014/0235823 A1 | 8/2014 | Kong | |

OTHER PUBLICATIONS

Coral Gonza' lez-Prieto1 et al, HUH site-specific recombinases for targeted modification of the human genome Trends in Biotechnology May 2013, vol. 31, No. 5, 2013.*
Wishart et al., (J. Biol. Chem., 1995, vol. 270(10): 26782-26785) (Year: 1995).*
Witkowski et al (Conversion of a beta-ketoacyl synthase to a malonyl decarboxylase by replacement of the active-site cysteine with glutamine. Biochemistry 38:11643-11650, 1999 (Year: 1999).*
Broun et ah, (Science 282:1315-1317, 1998), (Year: 1998).*
Boer, "Plasmid replication initiator RepB forms a hexamer reminiscent of ring helicases and has mobile nuclease domains" 2009 *EMBO J.* 28, 1666-1678.
Chandler, "Breaking and joining single-stranded DNA: the HUH endonuclease superfamily" Aug. 2013 *Nature Rev. Microbiol.*, 11:525-538.
Datta, "Structural insights into single-stranded DNA binding and cleavage by F factor TraI" Nov. 2003 *Structure/Folding and Design*, 11:1369-1379.
Derr, "Tug-of-war in motor protein ensembles revealed with a programmable DNA origami scaffold" Nov. 2012 *Science*, 338(6107):662-665.
Edwards, "Molecular basis of antibiotic multiresistance transfer in *Staphylococcus aureus*" Feb. 2013 *Proceedings of the National Academy of Sciences*, 110(8):2804-2809.
Fu, "Multi-enzyme complexes on DNA scaffolds capable of substrate channelling with an artificial swinging arm" Jul. 2014 *Nat Nanotechnol.*, 9(7):531-6. doi:10.1038/nnano.2014.100.
Gautier, "An Engineered Protein Tag for Multiprotein Labeling in Living Cells" Feb. 2008 *Chem Biol.*, 15(2):128-36.
Gordon, "Mechanical Allostery: Evidence for a Force Requirement in the Proteolytic Activation of Notch" Jun. 2015 *Developmental Cell*, 33(6):729-736. doi:10.1016/j.devcel.2015.05.004.
Halvorsen, "Nanoengineering a single-molecule mechanical switch using DNA self-assembly" Dec. 2011 *Nanotechnology*, 22(49):494005.
Hariadi, "Myosin lever arm directs collective motion on cellular actin network" 2014 *Proceedings of the National Academy of Sciences*, 111(11):4091-4096.
Harley, "Swapping single-stranded DNA sequence specificities of relaxases from conjugative plasmids F and R100" Sep. 2003 *Proceedings of the National Academy of Sciences*, 100(20): 11243-11248.
Jungmann, "Multiplexed 3D cellular super-resolution imaging with DNA-PAINT and Exchange-PAINT" Mar. 2014 *Nature Methods*, 11(3):313-318.
Keppler, "Labeling of fusion proteins of O6-alkylguanine-DNA alkyltransferase with small molecules in vivo and in vitro" Apr. 2004 *Methods*, 32(4):437-44.
Keppler, "A general method for the covalent labeling of fusion proteins with small molecules in vivo" 2002 *Nat Biotechnol.*, 21:86-89.
Liu, "Aptamer-directed self-assembly of protein arrays on a DNA nanostructure" Jul. 2005 *Angew Chem. Int. Ed. Engl.*, 44(28):4333-4338.
Los, "HaloTag: a novel protein labeling technology for cell imaging and protein analysis" Jun. 2008 *ACS Chem. Biol.*, 3(6):373-382.

(Continued)

*Primary Examiner* — Kagnew H Gebreyesus
(74) *Attorney, Agent, or Firm* — Mueting, Raasch & Gebhardt, P.A.

(57) ABSTRACT

This disclosure describes fusion polypeptides and complexes, compositions, and methods involving the fusion polypeptides. Generally, the fusion polypeptides include at least a portion of a protein of interest and at least a functional portion of a HUH polypeptide. Generally, the functional portion of a HUH polypeptide includes at least a portion of a Rep/relaxase domain that includes at least one catalytic polar amino acid residue and at least one metal-coordinating amino acid residues.

9 Claims, 6 Drawing Sheets
(6 of 6 Drawing Sheet(s) Filed in Color)
Specification includes a Sequence Listing.

(56) References Cited

OTHER PUBLICATIONS

Mali, "Barcoding cells using cell-surface programmable DNA-binding domains" May 2013 *Nature Methods*, 10(5):403-406.
Monzingo, "The structure of the minimal relaxase domain of MobA at 2.1 A resolution" Feb. 2007 *J. Mol. Biol.*, 366(1):165-178.
Nakata, "Zinc-finger proteins for site-specific protein positioning on DNA-origami structures" Mar. 2012 *Angew. Chem. Int. Ed. Engl.*, 51(10):2421-2424.
Shaw, "Spatial control of membrane receptor function using ligand nanocalipers" Jul. 2014 *Nature Methods*, 11:841-846.
Söderberg, "Direct observation of individual endogenous protein complexes in situ by proximity ligation" Dec. 2006 *Nature Methods*, 3(12):995-1000.
Stephanopoulos, "Choosing an effective protein bioconjugation strategy" Nov. 2011 *Nat. Chem. Biol.*, 7(12):876-884.
Stern, "DNA recognition by F factor TraI36: highly sequence-specific binding of single-stranded DNA" Sep. 2001 *Biochemistry*, 40(38):11586-95.
Urh, "HaloTag, a Platform Technology for Protein Analysis" Dec. 2012 *Curr. Chem. Genomics*, 6:72-78.
Vega-Rocha, "Solution Structure of the Endonuclease Domain from the Master Replication Initiator Protein of the Nanovirus Faba Bean Necrotic Yellows Virus and Comparison with the corresponding Geminivirus and Circovirus Structures" May 2007 *Biochemistry*, 46(21): 6201-6212. doi: 10.1021/bi700159q. PMCID: PMC2577285. NIHMSID: NIHMS62345.
Vega-Rocha, "Solution structure, divalent metal and DNA binding of the endonuclease domain from the replication initiation protein from porcine circovirus 2" Mar. 2007 *J. Mol. Biol.*, 367(2):473-487.
Yano, "Tag—probe labeling methods for live-cell imaging of membrane proteins" Oct. 2009 *BBA Biomembranes*, 1788(10):2124-2131.

\* cited by examiner

SEQUENCE LISTING

<160> NUMBER OF SEQ ID NOS: 21

<210> SEQ ID NO 1
<211> LENGTH: 110
<212> TYPE: PRT
<213> ORGANISM: Artificial Sequence
<220> FEATURE:
<223> OTHER INFORMATION: synthetic polypeptide

<400> SEQUENCE: 1

```
Met Arg Gly Ser His His His His His His Met Ala Ser Gly Ser Asp
1               5                   10                  15

Ser Glu Val Asn Gln Glu Ala Lys Pro Glu Val Lys Pro Glu Val Lys
            20                  25                  30

Pro Glu Thr His Ile Asn Leu Lys Val Ser Asp Gly Ser Ser Glu Ile
        35                  40                  45

Phe Phe Lys Ile Lys Lys Thr Thr Pro Leu Arg Arg Leu Met Glu Ala
```

```
            50                  55                  60
Phe Ala Lys Arg Gln Gly Lys Glu Met Asp Ser Leu Arg Phe Leu Tyr
 65                  70                  75                  80

Asp Gly Ile Arg Ile Gln Ala Asp Gln Thr Pro Glu Asp Leu Asp Met
                 85                  90                  95

Glu Asp Asn Asp Ile Ile Glu Ala His Arg Glu Gln Ile Gly
                100                 105                 110

<210> SEQ ID NO 2
<211> LENGTH: 116
<212> TYPE: PRT
<213> ORGANISM: Porcine circovirus 2

<400> SEQUENCE: 2

Ser Pro Ser Lys Lys Asn Gly Arg Ser Gly Pro Gln Pro His Lys Arg
 1               5                  10                  15

Trp Val Phe Thr Leu Asn Asn Pro Ser Glu Asp Glu Arg Lys Lys Ile
                20                  25                  30

Arg Asp Leu Pro Ile Ser Leu Phe Asp Tyr Phe Ile Val Gly Glu Glu
                35                  40                  45

Gly Asn Glu Glu Gly Arg Thr Pro His Leu Gln Gly Phe Ala Asn Phe
 50                  55                  60

Val Lys Lys Gln Thr Phe Asn Lys Val Lys Trp Tyr Leu Gly Ala Arg
 65                  70                  75                  80

Cys His Ile Glu Lys Ala Lys Gly Thr Asp Gln Gln Asn Lys Glu Tyr
                85                  90                  95

Cys Ser Lys Glu Gly Asn Leu Leu Met Glu Cys Gly Ala Pro Arg Ser
                100                 105                 110

Gln Gly Gln Arg
        115

<210> SEQ ID NO 3
<211> LENGTH: 340
<212> TYPE: PRT
<213> ORGANISM: PhiX174

<400> SEQUENCE: 3

Lys Ser Arg Arg Gly Phe Ala Ile Gln Arg Leu Met Asn Ala Met Arg
 1               5                  10                  15

Gln Ala His Ala Asp Gly Trp Phe Ile Val Phe Asp Thr Leu Thr Leu
                20                  25                  30

Ala Asp Asp Arg Leu Glu Ala Phe Tyr Asp Asn Pro Asn Ala Leu Arg
                35                  40                  45

Asp Tyr Phe Arg Asp Ile Gly Arg Met Val Leu Ala Ala Glu Gly Arg
 50                  55                  60

Lys Ala Asn Asp Ser His Ala Asp Cys Tyr Gln Tyr Phe Cys Val Pro
 65                  70                  75                  80

Glu Tyr Gly Thr Ala Asn Gly Arg Leu His Phe His Ala Val His Phe
                85                  90                  95

Met Arg Thr Leu Pro Thr Gly Ser Val Asp Pro Asn Phe Gly Arg Arg
                100                 105                 110

Val Arg Asn Arg Arg Gln Leu Asn Ser Leu Gln Asn Thr Trp Pro Tyr
                115                 120                 125

Gly His Ser Met Pro Ile Ala Val Arg Tyr Thr Gln Asp Ala Phe Ser
        130                 135                 140

Arg Ser Gly Trp Leu Trp Pro Val Asp Ala Lys Gly Glu Pro Leu Lys
```

```
                    145                 150                 155                 160
Ala Thr Ser Tyr Met Ala Val Gly Phe Tyr Val Ala Lys Tyr Val Asn
                165                 170                 175
Lys Lys Ser Asp Met Asp Leu Ala Ala Lys Gly Leu Gly Ala Lys Glu
            180                 185                 190
Trp Asn Asn Ser Leu Lys Thr Lys Leu Ser Leu Pro Lys Lys Leu
        195                 200                 205
Phe Arg Ile Arg Met Ser Arg Asn Phe Gly Met Lys Met Leu Thr Met
    210                 215                 220
Thr Asn Leu Ser Thr Glu Cys Leu Ile Gln Leu Thr Lys Leu Gly Tyr
225                 230                 235                 240
Asp Ala Thr Pro Phe Asn Gln Ile Leu Lys Gln Asn Ala Lys Arg Glu
                245                 250                 255
Met Arg Leu Arg Leu Gly Lys Val Thr Val Ala Asp Val Leu Ala Ala
            260                 265                 270
Gln Pro Val Thr Thr Asn Leu Leu Lys Phe Met Arg Ala Ser Ile Lys
        275                 280                 285
Met Ile Gly Val Ser Asn Leu Gln Ser Phe Ile Ala Ser Met Thr Gln
    290                 295                 300
Lys Leu Thr Leu Ser Asp Ile Ser Asp Glu Ser Lys Asn Tyr Leu Asp
305                 310                 315                 320
Lys Ala Gly Ile Thr Thr Ala Cys Leu Arg Ile Lys Ser Lys Trp Thr
                325                 330                 335
Ala Gly Gly Lys
            340

<210> SEQ ID NO 4
<211> LENGTH: 186
<212> TYPE: PRT
<213> ORGANISM: E. coli

<400> SEQUENCE: 4

Met Ala Ile Tyr His Leu Thr Ala Lys Thr Gly Ser Arg Ser Gly Gly
1               5                   10                  15
Gln Ser Ala Arg Ala Lys Ala Asp Tyr Ile Gln Arg Glu Gly Lys Tyr
            20                  25                  30
Ala Arg Asp Met Asp Glu Val Leu His Ala Glu Ser Gly His Met Pro
        35                  40                  45
Glu Phe Val Glu Arg Pro Ala Asp Tyr Trp Asp Ala Ala Asp Leu Tyr
    50                  55                  60
Glu Arg Ala Asn Gly Arg Leu Phe Lys Glu Val Glu Phe Ala Leu Pro
65                  70                  75                  80
Val Glu Leu Thr Leu Asp Gln Gln Lys Ala Leu Ala Ser Glu Phe Ala
                85                  90                  95
Gln His Leu Thr Gly Ala Glu Arg Leu Pro Tyr Thr Leu Ala Ile His
            100                 105                 110
Ala Gly Gly Gly Glu Asn Pro His Cys His Leu Met Ile Ser Glu Arg
        115                 120                 125
Ile Asn Asp Gly Ile Glu Arg Pro Ala Ala Gln Trp Phe Lys Arg Tyr
    130                 135                 140
Asn Gly Lys Thr Pro Glu Lys Gly Gly Ala Gln Lys Thr Glu Ala Leu
145                 150                 155                 160
Lys Pro Lys Ala Trp Leu Glu Gln Thr Arg Glu Ala Trp Ala Asp His
                165                 170                 175
```

Ala Asn Arg Ala Leu Glu Arg Ala Gly His
            180                 185

<210> SEQ ID NO 5
<211> LENGTH: 330
<212> TYPE: PRT
<213> ORGANISM: E. coli

<400> SEQUENCE: 5

Met Met Ser Ile Ala Gln Val Arg Ser Ala Gly Ser Ala Gly Asn Tyr
1               5                   10                  15

Tyr Thr Asp Lys Asp Asn Tyr Tyr Val Leu Gly Ser Met Gly Glu Arg
            20                  25                  30

Trp Ala Gly Arg Gly Ala Glu Gln Leu Gly Leu Gln Gly Ser Val Asp
        35                  40                  45

Lys Asp Val Phe Thr Arg Leu Leu Glu Gly Arg Leu Pro Asp Gly Ala
50                  55                  60

Asp Leu Ser Arg Met Gln Asp Gly Ser Asn Arg His Arg Pro Gly Tyr
65                  70                  75                  80

Asp Leu Thr Phe Ser Ala Pro Lys Ser Val Ser Met Met Ala Met Leu
                85                  90                  95

Gly Gly Asp Lys Arg Leu Ile Asp Ala His Asn Gln Ala Val Asp Phe
            100                 105                 110

Ala Val Arg Gln Val Glu Ala Leu Ala Ser Thr Arg Val Met Thr Asp
        115                 120                 125

Gly Gln Ser Glu Thr Val Leu Thr Gly Asn Leu Val Met Ala Leu Phe
    130                 135                 140

Asn His Asp Thr Ser Arg Asp Gln Glu Pro Gln Leu His Thr His Ala
145                 150                 155                 160

Val Val Ala Asn Val Thr Gln His Asn Gly Glu Trp Lys Thr Leu Ser
                165                 170                 175

Ser Asp Lys Val Gly Lys Thr Gly Phe Ile Glu Asn Val Tyr Ala Asn
            180                 185                 190

Gln Ile Ala Phe Gly Arg Leu Tyr Arg Glu Lys Leu Lys Glu Gln Val
        195                 200                 205

Glu Ala Leu Gly Tyr Glu Thr Glu Val Val Gly Lys His Gly Met Trp
    210                 215                 220

Glu Met Pro Gly Val Pro Val Glu Ala Phe Ser Gly Arg Ser Gln Thr
225                 230                 235                 240

Ile Arg Glu Ala Val Gly Glu Asp Ala Ser Leu Lys Ser Arg Asp Val
                245                 250                 255

Ala Ala Leu Asp Thr Arg Lys Ser Lys Gln His Val Asp Pro Glu Ile
            260                 265                 270

Lys Met Ala Glu Trp Met Gln Thr Leu Lys Glu Thr Gly Phe Asp Ile
        275                 280                 285

Arg Ala Tyr Arg Asp Ala Ala Asp Gln Arg Ala Asp Leu Arg Thr Leu
    290                 295                 300

Thr Pro Gly Pro Ala Ser Gln Asp Gly Pro Asp Val Gln Gln Ala Val
305                 310                 315                 320

Thr Gln Ala Ile Ala Gly Leu Ser Glu Arg
                325                 330

<210> SEQ ID NO 6
<211> LENGTH: 133
<212> TYPE: PRT
<213> ORGANISM: Streptococcus agalactiae

```
<400> SEQUENCE: 6

Met Ala Lys Glu Lys Ala Arg Tyr Phe Thr Phe Leu Leu Tyr Pro Glu
1               5                   10                  15

Ser Ile Pro Ser Asp Trp Glu Leu Lys Leu Glu Thr Leu Gly Val Pro
            20                  25                  30

Met Ala Ile Ser Pro Leu His Asp Lys Asp Lys Ser Ser Ile Lys Gly
        35                  40                  45

Gln Lys Tyr Lys Lys Ala His Tyr His Val Leu Tyr Ile Ala Lys Asn
    50                  55                  60

Pro Val Thr Ala Asp Ser Val Arg Lys Ile Lys Leu Leu Leu Gly
65                  70                  75                  80

Glu Lys Ser Leu Ala Met Val Gln Val Val Leu Asn Val Glu Asn Met
                85                  90                  95

Tyr Leu Tyr Leu Thr His Glu Ser Lys Asp Ala Ile Ala Lys Lys Lys
            100                 105                 110

His Val Tyr Asp Lys Ala Asp Ile Lys Leu Ile Asn Asn Phe Asp Ile
        115                 120                 125

Asp Arg Tyr Leu Glu
    130

<210> SEQ ID NO 7
<211> LENGTH: 98
<212> TYPE: PRT
<213> ORGANISM: Fava bean necrotic yellows virus (isolate Egyptian
      EV1-93)

<400> SEQUENCE: 7

Met Ala Arg Gln Val Ile Cys Trp Cys Phe Thr Leu Asn Asn Pro Leu
1               5                   10                  15

Ser Pro Leu Ser Leu His Asp Ser Met Lys Tyr Leu Val Tyr Gln Thr
            20                  25                  30

Glu Gln Gly Glu Ala Gly Asn Ile His Phe Gln Gly Tyr Ile Glu Met
        35                  40                  45

Lys Lys Arg Thr Ser Leu Ala Gly Met Lys Lys Leu Ile Pro Gly Ala
    50                  55                  60

His Phe Glu Lys Arg Arg Gly Thr Gln Gly Glu Ala Arg Ala Tyr Ser
65                  70                  75                  80

Met Lys Glu Asp Thr Arg Leu Glu Gly Pro Trp Glu Tyr Gly Glu Phe
                85                  90                  95

Val Pro

<210> SEQ ID NO 8
<211> LENGTH: 219
<212> TYPE: PRT
<213> ORGANISM: Staphylococcus aureus

<400> SEQUENCE: 8

Ala Met Tyr His Phe Gln Asn Lys Phe Val Ser Lys Ala Asn Gly Gln
1               5                   10                  15

Ser Ala Thr Ala Lys Ser Ala Tyr Asn Ser Ala Ser Arg Ile Lys Asp
            20                  25                  30

Phe Lys Glu Asn Glu Phe Lys Asp Tyr Ser Asn Lys Gln Cys Asp Tyr
        35                  40                  45

Ser Glu Ile Leu Leu Pro Asn Asn Ala Asp Asp Lys Phe Lys Asp Arg
    50                  55                  60
```

```
Glu Tyr Leu Trp Asn Lys Val His Asp Val Glu Asn Arg Lys Asn Ser
 65                  70                  75                  80

Gln Val Ala Arg Glu Ile Ile Ile Gly Leu Pro Asn Glu Phe Asp Pro
                 85                  90                  95

Asn Ser Asn Ile Glu Leu Ala Lys Glu Phe Ala Glu Ser Leu Ser Asn
            100                 105                 110

Glu Gly Met Ile Val Asp Leu Asn Ile His Lys Ile Asn Glu Glu Asn
        115                 120                 125

Pro His Ala His Leu Leu Cys Thr Leu Arg Gly Leu Asp Lys Asn Asn
    130                 135                 140

Glu Phe Glu Pro Lys Arg Lys Gly Asn Asp Tyr Ile Arg Asp Trp Asn
145                 150                 155                 160

Thr Lys Glu Lys His Asn Glu Trp Arg Lys Arg Trp Glu Asn Val Gln
                165                 170                 175

Asn Lys His Leu Glu Lys Asn Gly Phe Ser Val Arg Val Ser Ala Asp
            180                 185                 190

Ser Tyr Lys Asn Gln Asn Ile Asp Leu Glu Pro Thr Lys Lys Glu Gly
        195                 200                 205

Trp Lys Ala Arg Lys Phe Glu Asp Glu Thr Gly
    210                 215

<210> SEQ ID NO 9
<211> LENGTH: 293
<212> TYPE: PRT
<213> ORGANISM: E. coli

<400> SEQUENCE: 9

Met Leu Ser His Met Val Leu Thr Arg Gln Asp Ile Gly Arg Ala Ala
1               5                   10                  15

Ser Tyr Tyr Glu Asp Gly Ala Asp Tyr Tyr Ala Lys Asp Gly Asp
            20                  25                  30

Ala Ser Glu Trp Gln Gly Lys Gly Ala Glu Glu Leu Gly Leu Ser Gly
        35                  40                  45

Glu Val Asp Ser Lys Arg Phe Arg Glu Leu Leu Ala Gly Asn Ile Gly
 50                  55                  60

Glu Gly His Arg Ile Met Arg Ser Ala Thr Arg Gln Asp Ser Lys Glu
 65                  70                  75                  80

Arg Ile Gly Leu Asp Leu Thr Phe Ser Ala Pro Lys Ser Val Ser Leu
                 85                  90                  95

Gln Ala Leu Val Ala Gly Asp Ala Glu Ile Ile Lys Ala His Asp Arg
            100                 105                 110

Ala Val Ala Arg Thr Leu Glu Gln Ala Glu Ala Arg Ala Gln Ala Arg
        115                 120                 125

Gln Lys Ile Gln Gly Lys Thr Arg Ile Glu Thr Thr Gly Asn Leu Val
    130                 135                 140

Ile Gly Lys Phe Arg His Glu Thr Ser Arg Glu Arg Asp Pro Gln Leu
145                 150                 155                 160

His Thr His Ala Val Ile Leu Asn Met Thr Lys Arg Ser Asp Gly Gln
                165                 170                 175

Trp Arg Ala Leu Lys Asn Asp Glu Ile Val Lys Ala Thr Arg Tyr Leu
            180                 185                 190

Gly Ala Val Tyr Asn Ala Glu Leu Ala His Glu Leu Gln Lys Leu Gly
        195                 200                 205

Tyr Gln Leu Arg Tyr Gly Lys Asp Gly Asn Phe Asp Leu Ala His Ile
    210                 215                 220
```

Asp Arg Gln Gln Ile Glu Gly Phe Ser Lys Arg Thr Glu Gln Ile Ala
225                 230                 235                 240

Glu Trp Tyr Ala Ala Arg Gly Leu Asp Pro Asn Ser Val Ser Leu Glu
            245                 250                 255

Gln Lys Gln Ala Ala Lys Val Leu Ser Arg Ala Lys Thr Ser Val
        260                 265                 270

Asp Arg Glu Ala Leu Arg Ala Glu Trp Gln Ala Thr Ala Lys Glu Leu
        275                 280                 285

Gly Ile Asp Phe Ser
        290

<210> SEQ ID NO 10
<211> LENGTH: 120
<212> TYPE: PRT
<213> ORGANISM: Tomato yellow leaf curl virus (strain Israel)

<400> SEQUENCE: 10

Met Pro Arg Leu Phe Lys Ile Tyr Ala Lys Asn Tyr Phe Leu Thr Tyr
1               5                   10                  15

Pro Asn Cys Ser Leu Ser Lys Glu Glu Ala Leu Ser Gln Leu Lys Lys
            20                  25                  30

Leu Glu Thr Pro Thr Asn Lys Lys Tyr Ile Lys Val Cys Lys Glu Leu
        35                  40                  45

His Glu Asn Gly Glu Pro His Leu His Val Leu Ile Gln Phe Glu Gly
    50                  55                  60

Lys Tyr Gln Cys Lys Asn Gln Arg Phe Phe Asp Leu Val Ser Pro Asn
65                  70                  75                  80

Arg Ser Ala His Phe His Pro Asn Ile Gln Ala Ala Lys Ser Ser Thr
                85                  90                  95

Asp Val Lys Thr Tyr Val Glu Lys Asp Gly Asn Phe Ile Asp Phe Gly
            100                 105                 110

Val Ser Gln Ile Asp Gly Arg Ser
        115                 120

<210> SEQ ID NO 11
<211> LENGTH: 31
<212> TYPE: DNA
<213> ORGANISM: Artificial Sequence
<220> FEATURE:
<223> OTHER INFORMATION: synthetic polynucleotide
<220> FEATURE:
<221> NAME/KEY: nick_site
<222> LOCATION: (12)..(13)

<400> SEQUENCE: 11
tcgacaactt gatattaata acactataga c                                      31

<210> SEQ ID NO 12
<211> LENGTH: 12
<212> TYPE: DNA
<213> ORGANISM: Artificial Sequence
<220> FEATURE:
<223> OTHER INFORMATION: synthetic polynucleotide
<220> FEATURE:
<221> NAME/KEY: nick_site
<222> LOCATION: (7)..(8)

<400> SEQUENCE: 12
aagtattacc ag                                                           12

<210> SEQ ID NO 13
<211> LENGTH: 22
<212> TYPE: DNA
<213> ORGANISM: Artificial Sequence
<220> FEATURE:
<223> OTHER INFORMATION: synthetic polynucleotide
<220> FEATURE:
<221> NAME/KEY: nick_site
<222> LOCATION: (14)..(15)

<400> SEQUENCE: 13
tttgcgtggg gtgtggtgct tt                                    22

<210> SEQ ID NO 14
<211> LENGTH: 35
<212> TYPE: DNA
<213> ORGANISM: Artificial Sequence
<220> FEATURE:
<223> OTHER INFORMATION: synthetic polynucleotide
<220> FEATURE:
<221> NAME/KEY: nick_site
<222> LOCATION: (31)..(32)

<400> SEQUENCE: 14
ccagtttctc gaagagaaac cggtaaatgc gccct                      35

<210> SEQ ID NO 15
<211> LENGTH: 23
<212> TYPE: DNA
<213> ORGANISM: Artificial Sequence
<220> FEATURE:
<223> OTHER INFORMATION: synthetic polynucleotide
<220> FEATURE:
<221> NAME/KEY: nick_site
<222> LOCATION: (15)..(16)

<400> SEQUENCE: 15
tgcttccgta ctacgacccc cca                                   23

<210> SEQ ID NO 16
<211> LENGTH: 2471
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (35)..(221)
<223> OTHER INFORMATION: mMobA

<400> SEQUENCE: 16

```
Met Pro Pro Leu Leu Ala Pro Leu Leu Cys Leu Ala Leu Leu Pro Ala
1               5                   10                  15

Leu Ala Ala Arg Gly Ser Gly Asp Tyr Lys Asp Asp Asp Lys Gly
            20                  25                  30

Thr Gly Gly Met Ala Ile Tyr His Leu Thr Ala Lys Thr Gly Ser Arg
        35                  40                  45

Ser Gly Gly Gln Ser Ala Arg Ala Lys Ala Asp Tyr Ile Gln Arg Glu
    50                  55                  60

Gly Lys Tyr Ala Arg Asp Met Asp Glu Val Leu His Ala Glu Ser Gly
65                  70                  75                  80

His Met Pro Glu Phe Val Glu Arg Pro Ala Asp Tyr Trp Asp Ala Ala
                85                  90                  95

Asp Leu Tyr Glu Arg Ala Asn Gly Arg Leu Phe Lys Glu Val Glu Phe
            100                 105                 110
```

```
Ala Leu Pro Val Glu Leu Thr Leu Asp Gln Gln Lys Ala Leu Ala Ser
            115                 120                 125

Glu Phe Ala Gln His Leu Thr Gly Ala Glu Arg Leu Pro Tyr Thr Leu
    130                 135                 140

Ala Ile His Ala Gly Gly Glu Asn Pro His Cys His Leu Met Ile
145                 150                 155                 160

Ser Glu Arg Ile Asn Asp Gly Ile Glu Arg Pro Ala Ala Gln Trp Phe
                165                 170                 175

Lys Arg Tyr Asn Gly Lys Thr Pro Glu Lys Gly Ala Gln Lys Thr
            180                 185                 190

Glu Ala Leu Lys Pro Lys Ala Trp Leu Glu Gln Thr Arg Glu Ala Trp
        195                 200                 205

Ala Asp His Ala Asn Arg Ala Leu Glu Arg Ala Gly His Gly Ser Gly
    210                 215                 220

Thr Cys Ser Gln Pro Gly Glu Thr Cys Leu Asn Gly Gly Lys Cys Glu
225                 230                 235                 240

Ala Ala Asn Gly Thr Glu Ala Cys Val Cys Gly Gly Ala Phe Val Gly
                245                 250                 255

Pro Arg Cys Gln Asp Pro Asn Pro Cys Leu Ser Thr Pro Cys Lys Asn
        260                 265                 270

Ala Gly Thr Cys His Val Val Asp Arg Arg Gly Val Ala Asp Tyr Ala
    275                 280                 285

Cys Ser Cys Ala Leu Gly Phe Ser Gly Pro Leu Cys Leu Thr Pro Leu
    290                 295                 300

Asp Asn Ala Cys Leu Thr Asn Pro Cys Arg Asn Gly Gly Thr Cys Asp
305                 310                 315                 320

Leu Leu Thr Leu Thr Glu Tyr Lys Cys Arg Cys Pro Pro Gly Trp Ser
                325                 330                 335

Gly Lys Ser Cys Gln Gln Ala Asp Pro Cys Ala Ser Asn Pro Cys Ala
            340                 345                 350

Asn Gly Gly Gln Cys Leu Pro Phe Glu Ala Ser Tyr Ile Cys His Cys
        355                 360                 365

Pro Pro Ser Phe His Gly Pro Thr Cys Arg Gln Asp Val Asn Glu Cys
    370                 375                 380

Gly Gln Lys Pro Gly Leu Cys Arg His Gly Gly Thr Cys His Asn Glu
385                 390                 395                 400

Val Gly Ser Tyr Arg Cys Val Cys Arg Ala Thr His Thr Gly Pro Asn
                405                 410                 415

Cys Glu Arg Pro Tyr Val Pro Cys Ser Pro Ser Pro Cys Gln Asn Gly
        420                 425                 430

Gly Thr Cys Arg Pro Thr Gly Asp Val Thr His Glu Cys Ala Cys Leu
    435                 440                 445

Pro Gly Phe Thr Gly Gln Asn Cys Glu Glu Asn Ile Asp Asp Cys Pro
450                 455                 460

Gly Asn Asn Cys Lys Asn Gly Gly Ala Cys Val Asp Gly Val Asn Thr
465                 470                 475                 480

Tyr Asn Cys Arg Cys Pro Pro Glu Trp Thr Gly Gln Tyr Cys Thr Glu
                485                 490                 495

Asp Val Asp Glu Cys Gln Leu Met Pro Asn Ala Cys Gln Asn Gly Gly
        500                 505                 510

Thr Cys His Asn Thr His Gly Gly Tyr Asn Cys Val Cys Val Asn Gly
    515                 520                 525

Trp Thr Gly Glu Asp Cys Ser Glu Asn Ile Asp Asp Cys Ala Ser Ala
```

```
                530             535             540
Ala Cys Phe His Gly Ala Thr Cys His Asp Arg Val Ala Ser Phe Tyr
545                 550                 555                 560

Cys Glu Cys Pro His Gly Arg Thr Gly Leu Leu Cys His Leu Asn Asp
                565                 570                 575

Ala Cys Ile Ser Asn Pro Cys Asn Glu Gly Ser Asn Cys Asp Thr Asn
                580                 585                 590

Pro Val Asn Gly Lys Ala Ile Cys Thr Cys Pro Ser Gly Tyr Thr Gly
                595                 600                 605

Pro Ala Cys Ser Gln Asp Val Asp Glu Cys Ser Leu Gly Ala Asn Pro
610                 615                 620

Cys Glu His Ala Gly Lys Cys Ile Asn Thr Leu Gly Ser Phe Glu Cys
625                 630                 635                 640

Gln Cys Leu Gln Gly Tyr Thr Gly Pro Arg Cys Glu Ile Asp Val Asn
                645                 650                 655

Glu Cys Val Ser Asn Pro Cys Gln Asn Asp Ala Thr Cys Leu Asp Gln
                660                 665                 670

Ile Gly Glu Phe Gln Cys Ile Cys Met Pro Gly Tyr Glu Gly Val His
                675                 680                 685

Cys Glu Val Asn Thr Asp Glu Cys Ala Ser Ser Pro Cys Leu His Asn
690                 695                 700

Gly Arg Cys Leu Asp Lys Ile Asn Glu Phe Gln Cys Glu Cys Pro Thr
705                 710                 715                 720

Gly Phe Thr Gly His Leu Cys Gln Tyr Asp Val Asp Glu Cys Ala Ser
                725                 730                 735

Thr Pro Cys Lys Asn Gly Ala Lys Cys Leu Asp Gly Pro Asn Thr Tyr
                740                 745                 750

Thr Cys Val Cys Thr Glu Gly Tyr Thr Gly Thr His Cys Glu Val Asp
                755                 760                 765

Ile Asp Glu Cys Asp Pro Asp Pro Cys His Tyr Gly Ser Cys Lys Asp
                770                 775                 780

Gly Val Ala Thr Phe Thr Cys Leu Cys Arg Pro Gly Tyr Thr Gly His
785                 790                 795                 800

His Cys Glu Thr Asn Ile Asn Glu Cys Ser Ser Gln Pro Cys Arg His
                805                 810                 815

Gly Gly Thr Cys Gln Asp Arg Asp Asn Ala Tyr Leu Cys Phe Cys Leu
                820                 825                 830

Lys Gly Thr Thr Gly Pro Asn Cys Glu Ile Asn Leu Asp Asp Cys Ala
                835                 840                 845

Ser Ser Pro Cys Asp Ser Gly Thr Cys Leu Asp Lys Ile Asp Gly Tyr
850                 855                 860

Glu Cys Ala Cys Glu Pro Gly Tyr Thr Gly Ser Met Cys Asn Ile Asn
865                 870                 875                 880

Ile Asp Glu Cys Ala Gly Asn Pro Cys His Asn Gly Gly Thr Cys Glu
                885                 890                 895

Asp Gly Ile Asn Gly Phe Thr Cys Arg Cys Pro Glu Gly Tyr His Asp
                900                 905                 910

Pro Thr Cys Leu Ser Glu Val Asn Glu Cys Asn Ser Asn Pro Cys Val
                915                 920                 925

His Gly Ala Cys Arg Asp Ser Leu Asn Gly Tyr Lys Cys Asp Cys Asp
                930                 935                 940

Pro Gly Trp Ser Gly Thr Asn Cys Asp Ile Asn Asn Glu Cys Glu
945                 950                 955                 960
```

-continued

Ser Asn Pro Cys Val Asn Gly Gly Thr Cys Lys Asp Met Thr Ser Gly
             965                 970                 975

Tyr Val Cys Thr Cys Arg Glu Gly Phe Ser Gly Pro Asn Cys Gln Thr
             980                 985                 990

Asn Ile Asn Glu Cys Ala Ser Asn Pro Cys Leu Asn Gln Gly Thr Cys
             995                1000                1005

Ile Asp Asp Val Ala Gly Tyr Lys Cys Asn Cys Leu Leu Pro Tyr
    1010                1015                1020

Thr Gly Ala Thr Cys Glu Val Val Leu Ala Pro Cys Ala Pro Ser
    1025                1030                1035

Pro Cys Arg Asn Gly Gly Glu Cys Arg Gln Ser Glu Asp Tyr Glu
    1040                1045                1050

Ser Phe Ser Cys Val Cys Pro Thr Gly Trp Gln Ala Gly Gln Thr
    1055                1060                1065

Cys Glu Val Asp Ile Asn Glu Cys Val Leu Ser Pro Cys Arg His
    1070                1075                1080

Gly Ala Ser Cys Gln Asn Thr His Gly Gly Tyr Arg Cys His Cys
    1085                1090                1095

Gln Ala Gly Tyr Ser Gly Arg Asn Cys Glu Thr Asp Ile Asp Asp
    1100                1105                1110

Cys Arg Pro Asn Pro Cys His Asn Gly Gly Ser Cys Thr Asp Gly
    1115                1120                1125

Ile Asn Thr Ala Phe Cys Asp Cys Leu Pro Gly Phe Arg Gly Thr
    1130                1135                1140

Phe Cys Glu Glu Asp Ile Asn Glu Cys Ala Ser Asp Pro Cys Arg
    1145                1150                1155

Asn Gly Ala Asn Cys Thr Asp Cys Val Asp Ser Tyr Thr Cys Thr
    1160                1165                1170

Cys Pro Ala Gly Phe Ser Gly Ile His Cys Glu Asn Asn Thr Pro
    1175                1180                1185

Asp Cys Thr Glu Ser Ser Cys Phe Asn Gly Gly Thr Cys Val Asp
    1190                1195                1200

Gly Ile Asn Ser Phe Thr Cys Leu Cys Pro Pro Gly Phe Thr Gly
    1205                1210                1215

Ser Tyr Cys Gln His Asp Val Asn Glu Cys Asp Ser Gln Pro Cys
    1220                1225                1230

Leu His Gly Gly Thr Cys Gln Asp Gly Cys Gly Ser Tyr Arg Cys
    1235                1240                1245

Thr Cys Pro Gln Gly Tyr Thr Gly Pro Asn Cys Gln Asn Leu Val
    1250                1255                1260

His Trp Cys Asp Ser Ser Pro Cys Lys Asn Gly Gly Lys Cys Trp
    1265                1270                1275

Gln Thr His Thr Gln Tyr Arg Cys Glu Cys Pro Ser Gly Trp Thr
    1280                1285                1290

Gly Leu Tyr Cys Asp Val Pro Ser Val Ser Cys Glu Val Ala Ala
    1295                1300                1305

Gln Arg Gln Gly Val Asp Val Ala Arg Leu Cys Gln His Gly Gly
    1310                1315                1320

Leu Cys Val Asp Ala Gly Asn Thr His His Cys Arg Cys Gln Ala
    1325                1330                1335

Gly Tyr Thr Gly Ser Tyr Cys Glu Asp Leu Val Asp Glu Cys Ser
    1340                1345                1350

-continued

Pro Ser Pro Cys Gln Asn Gly Ala Thr Cys Thr Asp Tyr Leu Gly
1355               1360                    1365

Gly Tyr Ser Cys Lys Cys Val Ala Gly Tyr His Gly Val Asn Cys
1370               1375                    1380

Ser Glu Glu Ile Asp Glu Cys Leu Ser His Pro Cys Gln Asn Gly
1385               1390                    1395

Gly Thr Cys Leu Asp Leu Pro Asn Thr Tyr Lys Cys Ser Cys Pro
1400               1405                    1410

Arg Gly Thr Gln Gly Val His Cys Glu Ile Asn Val Asp Asp Cys
1415               1420                    1425

Asn Pro Pro Val Asp Pro Val Ser Arg Ser Pro Lys Cys Phe Asn
1430               1435                    1440

Asn Gly Thr Cys Val Asp Gln Val Gly Gly Tyr Ser Cys Thr Cys
1445               1450                    1455

Pro Pro Gly Phe Val Gly Glu Arg Cys Glu Gly Asp Val Asn Glu
1460               1465                    1470

Cys Leu Ser Asn Pro Cys Asp Ala Arg Gly Thr Gln Asn Cys Val
1475               1480                    1485

Gln Arg Val Asn Asp Phe His Cys Glu Cys Arg Ala Gly His Thr
1490               1495                    1500

Gly Arg Arg Cys Glu Ser Val Ile Asn Gly Cys Lys Gly Lys Pro
1505               1510                    1515

Cys Lys Asn Gly Gly Thr Cys Ala Val Ala Ser Asn Thr Ala Arg
1520               1525                    1530

Gly Phe Ile Cys Lys Cys Pro Ala Gly Phe Glu Gly Ala Thr Cys
1535               1540                    1545

Glu Asn Asp Ala Arg Thr Cys Gly Ser Leu Arg Cys Leu Asn Gly
1550               1555                    1560

Gly Thr Cys Ile Ser Gly Pro Arg Ser Pro Thr Cys Leu Cys Leu
1565               1570                    1575

Gly Pro Phe Thr Gly Pro Glu Cys Gln Phe Pro Ala Ser Ser Pro
1580               1585                    1590

Cys Leu Gly Gly Asn Pro Cys Tyr Asn Gln Gly Thr Cys Glu Pro
1595               1600                    1605

Thr Ser Glu Ser Pro Phe Tyr Arg Cys Leu Cys Pro Ala Lys Phe
1610               1615                    1620

Asn Gly Leu Leu Cys His Ile Leu Asp Tyr Ser Phe Gly Gly Gly
1625               1630                    1635

Ala Gly Arg Asp Ile Pro Pro Pro Leu Ile Glu Glu Ala Cys Glu
1640               1645                    1650

Leu Pro Glu Cys Gln Glu Asp Ala Gly Asn Lys Val Cys Ser Leu
1655               1660                    1665

Gln Cys Asn Asn His Ala Cys Gly Trp Asp Gly Gly Asp Cys Ser
1670               1675                    1680

Leu Asn Phe Asn Asp Pro Trp Lys Asn Cys Thr Gln Ser Leu Gln
1685               1690                    1695

Cys Trp Lys Tyr Phe Ser Asp Gly His Cys Asp Ser Gln Cys Asn
1700               1705                    1710

Ser Ala Gly Cys Leu Phe Asp Gly Phe Asp Cys Gln Arg Ala Glu
1715               1720                    1725

Gly Gln Cys Asn Pro Leu Tyr Asp Gln Tyr Cys Lys Asp His Phe
1730               1735                    1740

Ser Asp Gly His Cys Asp Gln Gly Cys Asn Ser Ala Glu Cys Glu

```
              1745                1750                1755

Trp Asp Gly Leu Asp Cys Ala Glu His Val Pro Glu Arg Leu Ala
              1760                1765                1770

Ala Gly Thr Leu Val Val Val Leu Met Pro Pro Glu Gln Leu
              1775                1780                1785

Arg Asn Ser Ser Phe His Phe Leu Arg Glu Leu Ser Arg Val Leu
              1790                1795                1800

His Thr Asn Val Val Phe Lys Arg Asp Ala His Gly Gln Gln Met
              1805                1810                1815

Ile Phe Pro Tyr Tyr Gly Arg Glu Glu Glu Leu Arg Lys His Pro
              1820                1825                1830

Ile Lys Arg Ala Ala Glu Gly Trp Ala Ala Pro Asp Ala Leu Leu
              1835                1840                1845

Gly Gln Val Lys Ala Ser Leu Leu Pro Gly Gly Ser Glu Gly Gly
              1850                1855                1860

Arg Arg Arg Arg Glu Leu Asp Pro Met Asp Val Arg Gly Ser Ile
              1865                1870                1875

Val Tyr Leu Glu Ile Asp Asn Arg Gln Cys Val Gln Ala Ser Ser
              1880                1885                1890

Gln Cys Phe Gln Ser Ala Thr Asp Val Ala Ala Phe Leu Gly Ala
              1895                1900                1905

Leu Ala Ser Leu Gly Ser Leu Asn Ile Pro Tyr Lys Ile Glu Ala
              1910                1915                1920

Val Gln Ser Glu Thr Val Glu Pro Pro Pro Ala Gln Leu His
              1925                1930                1935

Phe Met Tyr Val Ala Ala Ala Phe Val Leu Leu Phe Phe Val
              1940                1945                1950

Gly Cys Gly Val Leu Leu Ser Arg Lys Arg Arg Gln His Gly
              1955                1960                1965

Gln Leu Trp Phe Pro Glu Val Lys Leu Leu Ser Ile Glu Gln
              1970                1975                1980

Ala Cys Asp Ile Cys Arg Leu Lys Lys Leu Lys Cys Ser Lys Glu
              1985                1990                1995

Lys Pro Lys Cys Ala Lys Cys Leu Lys Asn Asn Trp Glu Cys Arg
              2000                2005                2010

Tyr Ser Pro Lys Thr Lys Arg Ser Pro Leu Thr Arg Ala His Leu
              2015                2020                2025

Thr Glu Val Glu Ser Arg Leu Glu Arg Leu Glu Gln Leu Phe Leu
              2030                2035                2040

Leu Ile Phe Pro Arg Glu Asp Leu Asp Met Ile Leu Lys Met Asp
              2045                2050                2055

Ser Leu Gln Asp Ile Lys Ala Leu Leu Thr Gly Leu Phe Val Gln
              2060                2065                2070

Asp Asn Val Asn Lys Asp Ala Val Thr Asp Arg Leu Ala Ser Val
              2075                2080                2085

Glu Thr Asp Met Pro Leu Thr Leu Arg Gln His Arg Ile Ser Ala
              2090                2095                2100

Thr Ser Ser Ser Glu Glu Ser Asn Lys Gly Gln Arg Gln Leu
              2105                2110                2115

Thr Val Ser Pro His Gly Tyr Leu Ser Asp Val Ala Ser Pro Pro
              2120                2125                2130

Leu Leu Pro Ser Pro Phe Gln Gln Ser Pro Ser Val Pro Leu Asn
              2135                2140                2145
```

His Leu Pro Gly Met Pro Asp Thr His Leu Gly Ile Gly His Leu
    2150                2155                2160

Asn Val Ala Ala Lys Pro Glu Met Ala Ala Leu Gly Gly Gly Gly
    2165                2170                2175

Arg Leu Ala Phe Glu Thr Gly Pro Pro Arg Leu Ser His Leu Pro
    2180                2185                2190

Val Ala Ser Gly Thr Ser Thr Val Leu Gly Ser Ser Ser Gly Gly
    2195                2200                2205

Ala Leu Asn Phe Thr Val Gly Gly Ser Thr Ser Leu Asn Gly Gln
    2210                2215                2220

Cys Glu Trp Leu Ser Arg Leu Gln Ser Gly Met Val Pro Asn Gln
    2225                2230                2235

Tyr Asn Pro Leu Arg Gly Ser Val Ala Pro Gly Pro Leu Ser Thr
    2240                2245                2250

Gln Ala Pro Ser Leu Gln His Gly Met Val Gly Pro Leu His Ser
    2255                2260                2265

Ser Leu Ala Ala Ser Ala Leu Ser Gln Met Met Ser Tyr Gln Gly
    2270                2275                2280

Leu Pro Ser Thr Arg Leu Ala Thr Gln Pro His Leu Val Gln Thr
    2285                2290                2295

Gln Gln Val Gln Pro Gln Asn Leu Gln Met Gln Gln Gln Asn Leu
    2300                2305                2310

Gln Pro Ala Asn Ile Gln Gln Gln Ser Leu Gln Pro Pro Pro
    2315                2320                2325

Pro Pro Pro Gln Pro His Leu Gly Val Ser Ser Ala Ala Ser Gly
    2330                2335                2340

His Leu Gly Arg Ser Phe Leu Ser Gly Glu Pro Ser Gln Ala Asp
    2345                2350                2355

Val Gln Pro Leu Gly Pro Ser Ser Leu Ala Val His Thr Ile Leu
    2360                2365                2370

Pro Gln Glu Ser Pro Ala Leu Pro Thr Ser Leu Pro Ser Ser Leu
    2375                2380                2385

Val Pro Pro Val Thr Ala Ala Gln Phe Leu Thr Pro Pro Ser Gln
    2390                2395                2400

His Ser Tyr Ser Ser Pro Val Asp Asn Thr Pro Ser His Gln Leu
    2405                2410                2415

Gln Val Pro Glu His Pro Phe Leu Thr Pro Ser Pro Glu Ser Pro
    2420                2425                2430

Asp Gln Trp Ser Ser Ser Ser Pro His Ser Asn Val Ser Asp Trp
    2435                2440                2445

Ser Glu Gly Val Ser Ser Pro Pro Thr Ser Met Gln Ser Gln Ile
    2450                2455                2460

Ala Arg Ile Pro Glu Ala Phe Lys
    2465                2470

<210> SEQ ID NO 17
<211> LENGTH: 2615
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (38)..(367)
<223> OTHER INFORMATION: TraI36

<400> SEQUENCE: 17

```
Met Pro Pro Leu Leu Ala Pro Leu Leu Cys Leu Ala Leu Leu Pro Ala
1               5                   10                  15
Leu Ala Ala Arg Gly Ser Gly Asp Tyr Lys Asp Asp Asp Asp Lys Gly
            20                  25                  30
Thr Gly Ser Ser Gly Met Met Ser Ile Ala Gln Val Arg Ser Ala Gly
        35                  40                  45
Ser Ala Gly Asn Tyr Tyr Thr Asp Lys Asp Asn Tyr Tyr Val Leu Gly
    50                  55                  60
Ser Met Gly Glu Arg Trp Ala Gly Arg Gly Ala Glu Gln Leu Gly Leu
65                  70                  75                  80
Gln Gly Ser Val Asp Lys Asp Val Phe Thr Arg Leu Leu Glu Gly Arg
                85                  90                  95
Leu Pro Asp Gly Ala Asp Leu Ser Arg Met Gln Asp Gly Ser Asn Arg
            100                 105                 110
His Arg Pro Gly Tyr Asp Leu Thr Phe Ser Ala Pro Lys Ser Val Ser
        115                 120                 125
Met Met Ala Met Leu Gly Gly Asp Lys Arg Leu Ile Asp Ala His Asn
    130                 135                 140
Gln Ala Val Asp Phe Ala Val Arg Gln Val Glu Ala Leu Ala Ser Thr
145                 150                 155                 160
Arg Val Met Thr Asp Gly Gln Ser Glu Thr Val Leu Thr Gly Asn Leu
                165                 170                 175
Val Met Ala Leu Phe Asn His Asp Thr Ser Arg Asp Gln Glu Pro Gln
            180                 185                 190
Leu His Thr His Ala Val Val Ala Asn Val Thr Gln His Asn Gly Glu
        195                 200                 205
Trp Lys Thr Leu Ser Ser Asp Lys Val Gly Lys Thr Gly Phe Ile Glu
    210                 215                 220
Asn Val Tyr Ala Asn Gln Ile Ala Phe Gly Arg Leu Tyr Arg Glu Lys
225                 230                 235                 240
Leu Lys Glu Gln Val Glu Ala Leu Gly Tyr Glu Thr Glu Val Val Gly
                245                 250                 255
Lys His Gly Met Trp Glu Met Pro Gly Val Pro Val Glu Ala Phe Ser
            260                 265                 270
Gly Arg Ser Gln Thr Ile Arg Glu Ala Val Gly Glu Asp Ala Ser Leu
        275                 280                 285
Lys Ser Arg Asp Val Ala Ala Leu Asp Thr Arg Lys Ser Lys Gln His
    290                 295                 300
Val Asp Pro Glu Ile Lys Met Ala Glu Trp Met Gln Thr Leu Lys Glu
305                 310                 315                 320
Thr Gly Phe Asp Ile Arg Ala Tyr Arg Asp Ala Ala Asp Gln Arg Ala
                325                 330                 335
Asp Leu Arg Thr Leu Thr Pro Gly Pro Ala Ser Gln Asp Gly Pro Asp
            340                 345                 350
Val Gln Gln Ala Val Thr Gln Ala Ile Ala Gly Leu Ser Glu Arg Gly
        355                 360                 365
Thr Cys Ser Gln Pro Gly Glu Thr Cys Leu Asn Gly Gly Lys Cys Glu
    370                 375                 380
Ala Ala Asn Gly Thr Glu Ala Cys Val Cys Gly Gly Ala Phe Val Gly
385                 390                 395                 400
Pro Arg Cys Gln Asp Pro Asn Pro Cys Leu Ser Thr Pro Cys Lys Asn
                405                 410                 415
```

```
Ala Gly Thr Cys His Val Val Asp Arg Arg Gly Val Ala Asp Tyr Ala
            420             425             430

Cys Ser Cys Ala Leu Gly Phe Ser Gly Pro Leu Cys Leu Thr Pro Leu
        435             440             445

Asp Asn Ala Cys Leu Thr Asn Pro Cys Arg Asn Gly Gly Thr Cys Asp
    450             455             460

Leu Leu Thr Leu Thr Glu Tyr Lys Cys Arg Cys Pro Pro Gly Trp Ser
465             470             475             480

Gly Lys Ser Cys Gln Gln Ala Asp Pro Cys Ala Ser Asn Pro Cys Ala
            485             490             495

Asn Gly Gly Gln Cys Leu Pro Phe Glu Ala Ser Tyr Ile Cys His Cys
            500             505             510

Pro Pro Ser Phe His Gly Pro Thr Cys Arg Gln Asp Val Asn Glu Cys
            515             520             525

Gly Gln Lys Pro Gly Leu Cys Arg His Gly Gly Thr Cys His Asn Glu
            530             535             540

Val Gly Ser Tyr Arg Cys Val Cys Arg Ala Thr His Thr Gly Pro Asn
545             550             555             560

Cys Glu Arg Pro Tyr Val Pro Cys Ser Pro Ser Pro Cys Gln Asn Gly
                565             570             575

Gly Thr Cys Arg Pro Thr Gly Asp Val Thr His Glu Cys Ala Cys Leu
            580             585             590

Pro Gly Phe Thr Gly Gln Asn Cys Glu Glu Asn Ile Asp Asp Cys Pro
            595             600             605

Gly Asn Asn Cys Lys Asn Gly Gly Ala Cys Val Asp Gly Val Asn Thr
            610             615             620

Tyr Asn Cys Arg Cys Pro Pro Glu Trp Thr Gly Gln Tyr Cys Thr Glu
625             630             635             640

Asp Val Asp Glu Cys Gln Leu Met Pro Asn Ala Cys Gln Asn Gly Gly
                645             650             655

Thr Cys His Asn Thr His Gly Gly Tyr Asn Cys Val Cys Val Asn Gly
            660             665             670

Trp Thr Gly Glu Asp Cys Ser Glu Asn Ile Asp Asp Cys Ala Ser Ala
            675             680             685

Ala Cys Phe His Gly Ala Thr Cys His Asp Arg Val Ala Ser Phe Tyr
    690             695             700

Cys Glu Cys Pro His Gly Arg Thr Gly Leu Leu Cys His Leu Asn Asp
705             710             715             720

Ala Cys Ile Ser Asn Pro Cys Asn Glu Gly Ser Asn Cys Asp Thr Asn
            725             730             735

Pro Val Asn Gly Lys Ala Ile Cys Thr Cys Pro Ser Gly Tyr Thr Gly
            740             745             750

Pro Ala Cys Ser Gln Asp Val Asp Glu Cys Ser Leu Gly Ala Asn Pro
        755             760             765

Cys Glu His Ala Gly Lys Cys Ile Asn Thr Leu Gly Ser Phe Glu Cys
        770             775             780

Gln Cys Leu Gln Gly Tyr Thr Gly Pro Arg Cys Glu Ile Asp Val Asn
785             790             795             800

Glu Cys Val Ser Asn Pro Cys Gln Asn Asp Ala Thr Cys Leu Asp Gln
                805             810             815

Ile Gly Glu Phe Gln Cys Ile Cys Met Pro Gly Tyr Glu Gly Val His
            820             825             830
```

Cys Glu Val Asn Thr Asp Glu Cys Ala Ser Ser Pro Cys Leu His Asn
            835                 840                 845

Gly Arg Cys Leu Asp Lys Ile Asn Glu Phe Gln Cys Glu Cys Pro Thr
850                 855                 860

Gly Phe Thr Gly His Leu Cys Gln Tyr Asp Val Asp Glu Cys Ala Ser
865                 870                 875                 880

Thr Pro Cys Lys Asn Gly Ala Lys Cys Leu Asp Gly Pro Asn Thr Tyr
                885                 890                 895

Thr Cys Val Cys Thr Glu Gly Tyr Thr Gly Thr His Cys Glu Val Asp
            900                 905                 910

Ile Asp Glu Cys Asp Pro Asp Pro Cys His Tyr Gly Ser Cys Lys Asp
            915                 920                 925

Gly Val Ala Thr Phe Thr Cys Leu Cys Arg Pro Gly Tyr Thr Gly His
    930                 935                 940

His Cys Glu Thr Asn Ile Asn Glu Cys Ser Ser Gln Pro Cys Arg His
945                 950                 955                 960

Gly Gly Thr Cys Gln Asp Arg Asp Asn Ala Tyr Leu Cys Phe Cys Leu
            965                 970                 975

Lys Gly Thr Thr Gly Pro Asn Cys Glu Ile Asn Leu Asp Asp Cys Ala
            980                 985                 990

Ser Ser Pro Cys Asp Ser Gly Thr Cys Leu Asp Lys Ile Asp Gly Tyr
        995                 1000                1005

Glu Cys Ala Cys Glu Pro Gly Tyr Thr Gly Ser Met Cys Asn Ile
    1010                1015                1020

Asn Ile Asp Glu Cys Ala Gly Asn Pro Cys His Asn Gly Gly Thr
    1025                1030                1035

Cys Glu Asp Gly Ile Asn Gly Phe Thr Cys Arg Cys Pro Glu Gly
    1040                1045                1050

Tyr His Asp Pro Thr Cys Leu Ser Glu Val Asn Glu Cys Asn Ser
    1055                1060                1065

Asn Pro Cys Val His Gly Ala Cys Arg Asp Ser Leu Asn Gly Tyr
    1070                1075                1080

Lys Cys Asp Cys Asp Pro Gly Trp Ser Gly Thr Asn Cys Asp Ile
    1085                1090                1095

Asn Asn Asn Glu Cys Glu Ser Asn Pro Cys Val Asn Gly Gly Thr
    1100                1105                1110

Cys Lys Asp Met Thr Ser Gly Tyr Val Cys Thr Cys Arg Glu Gly
    1115                1120                1125

Phe Ser Gly Pro Asn Cys Gln Thr Asn Ile Asn Glu Cys Ala Ser
    1130                1135                1140

Asn Pro Cys Leu Asn Gln Gly Thr Cys Ile Asp Asp Val Ala Gly
    1145                1150                1155

Tyr Lys Cys Asn Cys Leu Leu Pro Tyr Thr Gly Ala Thr Cys Glu
    1160                1165                1170

Val Val Leu Ala Pro Cys Ala Pro Ser Pro Cys Arg Asn Gly Gly
    1175                1180                1185

Glu Cys Arg Gln Ser Glu Asp Tyr Glu Ser Phe Ser Cys Val Cys
    1190                1195                1200

Pro Thr Gly Trp Gln Ala Gly Gln Thr Cys Glu Val Asp Ile Asn
    1205                1210                1215

Glu Cys Val Leu Ser Pro Cys Arg His Gly Ala Ser Cys Gln Asn
    1220                1225                1230

Thr His Gly Gly Tyr Arg Cys His Cys Gln Ala Gly Tyr Ser Gly

```
                1235                1240                1245
Arg Asn Cys Glu Thr Asp Ile Asp Asp Cys Arg Pro Asn Pro Cys
    1250                1255                1260
His Asn Gly Gly Ser Cys Thr Asp Gly Ile Asn Thr Ala Phe Cys
    1265                1270                1275
Asp Cys Leu Pro Gly Phe Arg Gly Thr Phe Cys Glu Asp Ile
    1280                1285                1290
Asn Glu Cys Ala Ser Asp Pro Cys Arg Asn Gly Ala Asn Cys Thr
    1295                1300                1305
Asp Cys Val Asp Ser Tyr Thr Cys Thr Cys Pro Ala Gly Phe Ser
    1310                1315                1320
Gly Ile His Cys Glu Asn Asn Thr Pro Asp Cys Thr Glu Ser Ser
    1325                1330                1335
Cys Phe Asn Gly Gly Thr Cys Val Asp Gly Ile Asn Ser Phe Thr
    1340                1345                1350
Cys Leu Cys Pro Pro Gly Phe Thr Gly Ser Tyr Cys Gln His Asp
    1355                1360                1365
Val Asn Glu Cys Asp Ser Gln Pro Cys Leu His Gly Gly Thr Cys
    1370                1375                1380
Gln Asp Gly Cys Gly Ser Tyr Arg Cys Thr Cys Pro Gln Gly Tyr
    1385                1390                1395
Thr Gly Pro Asn Cys Gln Asn Leu Val His Trp Cys Asp Ser Ser
    1400                1405                1410
Pro Cys Lys Asn Gly Gly Lys Cys Trp Gln Thr His Thr Gln Tyr
    1415                1420                1425
Arg Cys Glu Cys Pro Ser Gly Trp Thr Gly Leu Tyr Cys Asp Val
    1430                1435                1440
Pro Ser Val Ser Cys Glu Val Ala Ala Gln Arg Gln Gly Val Asp
    1445                1450                1455
Val Ala Arg Leu Cys Gln His Gly Gly Leu Cys Val Asp Ala Gly
    1460                1465                1470
Asn Thr His His Cys Arg Cys Gln Ala Gly Tyr Thr Gly Ser Tyr
    1475                1480                1485
Cys Glu Asp Leu Val Asp Glu Cys Ser Pro Ser Pro Cys Gln Asn
    1490                1495                1500
Gly Ala Thr Cys Thr Asp Tyr Leu Gly Gly Tyr Ser Cys Lys Cys
    1505                1510                1515
Val Ala Gly Tyr His Gly Val Asn Cys Ser Glu Glu Ile Asp Glu
    1520                1525                1530
Cys Leu Ser His Pro Cys Gln Asn Gly Gly Thr Cys Leu Asp Leu
    1535                1540                1545
Pro Asn Thr Tyr Lys Cys Ser Cys Pro Arg Gly Thr Gln Gly Val
    1550                1555                1560
His Cys Glu Ile Asn Val Asp Asp Cys Asn Pro Val Asp Pro
    1565                1570                1575
Val Ser Arg Ser Pro Lys Cys Phe Asn Asn Gly Thr Cys Val Asp
    1580                1585                1590
Gln Val Gly Gly Tyr Ser Cys Thr Cys Pro Pro Gly Phe Val Gly
    1595                1600                1605
Glu Arg Cys Glu Gly Asp Val Asn Glu Cys Leu Ser Asn Pro Cys
    1610                1615                1620
Asp Ala Arg Gly Thr Gln Asn Cys Val Gln Arg Val Asn Asp Phe
    1625                1630                1635
```

```
His Cys Glu Cys Arg Ala Gly His Thr Gly Arg Arg Cys Glu Ser
1640                1645                1650

Val Ile Asn Gly Cys Lys Gly Lys Pro Cys Lys Asn Gly Gly Thr
1655                1660                1665

Cys Ala Val Ala Ser Asn Thr Ala Arg Gly Phe Ile Cys Lys Cys
1670                1675                1680

Pro Ala Gly Phe Glu Gly Ala Thr Cys Glu Asn Asp Ala Arg Thr
1685                1690                1695

Cys Gly Ser Leu Arg Cys Leu Asn Gly Gly Thr Cys Ile Ser Gly
1700                1705                1710

Pro Arg Ser Pro Thr Cys Leu Cys Leu Gly Pro Phe Thr Gly Pro
1715                1720                1725

Glu Cys Gln Phe Pro Ala Ser Ser Pro Cys Leu Gly Gly Asn Pro
1730                1735                1740

Cys Tyr Asn Gln Gly Thr Cys Glu Pro Thr Ser Glu Ser Pro Phe
1745                1750                1755

Tyr Arg Cys Leu Cys Pro Ala Lys Phe Asn Gly Leu Leu Cys His
1760                1765                1770

Ile Leu Asp Tyr Ser Phe Gly Gly Gly Ala Gly Arg Asp Ile Pro
1775                1780                1785

Pro Pro Leu Ile Glu Glu Ala Cys Glu Leu Pro Glu Cys Gln Glu
1790                1795                1800

Asp Ala Gly Asn Lys Val Cys Ser Leu Gln Cys Asn Asn His Ala
1805                1810                1815

Cys Gly Trp Asp Gly Gly Asp Cys Ser Leu Asn Phe Asn Asp Pro
1820                1825                1830

Trp Lys Asn Cys Thr Gln Ser Leu Gln Cys Trp Lys Tyr Phe Ser
1835                1840                1845

Asp Gly His Cys Asp Ser Gln Cys Asn Ser Ala Gly Cys Leu Phe
1850                1855                1860

Asp Gly Phe Asp Cys Gln Arg Ala Glu Gly Gln Cys Asn Pro Leu
1865                1870                1875

Tyr Asp Gln Tyr Cys Lys Asp His Phe Ser Asp Gly His Cys Asp
1880                1885                1890

Gln Gly Cys Asn Ser Ala Glu Cys Glu Trp Asp Gly Leu Asp Cys
1895                1900                1905

Ala Glu His Val Pro Glu Arg Leu Ala Ala Gly Thr Leu Val Val
1910                1915                1920

Val Val Leu Met Pro Pro Glu Gln Leu Arg Asn Ser Ser Phe His
1925                1930                1935

Phe Leu Arg Glu Leu Ser Arg Val Leu His Thr Asn Val Val Phe
1940                1945                1950

Lys Arg Asp Ala His Gly Gln Gln Met Ile Phe Pro Tyr Tyr Gly
1955                1960                1965

Arg Glu Glu Glu Leu Arg Lys His Pro Ile Lys Arg Ala Ala Glu
1970                1975                1980

Gly Trp Ala Ala Pro Asp Ala Leu Leu Gly Gln Val Lys Ala Ser
1985                1990                1995

Leu Leu Pro Gly Gly Ser Glu Gly Gly Arg Arg Arg Arg Glu Leu
2000                2005                2010

Asp Pro Met Asp Val Arg Gly Ser Ile Val Tyr Leu Glu Ile Asp
2015                2020                2025
```

```
Asn Arg Gln Cys Val Gln Ala Ser Ser Gln Cys Phe Gln Ser Ala
    2030            2035            2040

Thr Asp Val Ala Ala Phe Leu Gly Ala Leu Ala Ser Leu Gly Ser
    2045            2050            2055

Leu Asn Ile Pro Tyr Lys Ile Glu Ala Val Gln Ser Glu Thr Val
    2060            2065            2070

Glu Pro Pro Pro Ala Gln Leu His Phe Met Tyr Val Ala Ala
    2075            2080            2085

Ala Ala Phe Val Leu Leu Phe Val Gly Cys Gly Val Leu Leu
    2090            2095            2100

Ser Arg Lys Arg Arg Gln His Gly Gln Leu Trp Phe Pro Glu
    2105            2110            2115

Val Lys Leu Leu Ser Ser Ile Glu Gln Ala Cys Asp Ile Cys Arg
    2120            2125            2130

Leu Lys Lys Leu Lys Cys Ser Lys Glu Lys Pro Lys Cys Ala Lys
    2135            2140            2145

Cys Leu Lys Asn Asn Trp Glu Cys Arg Tyr Ser Pro Lys Thr Lys
    2150            2155            2160

Arg Ser Pro Leu Thr Arg Ala His Leu Thr Glu Val Glu Ser Arg
    2165            2170            2175

Leu Glu Arg Leu Glu Gln Leu Phe Leu Leu Ile Phe Pro Arg Glu
    2180            2185            2190

Asp Leu Asp Met Ile Leu Lys Met Asp Ser Leu Gln Asp Ile Lys
    2195            2200            2205

Ala Leu Leu Thr Gly Leu Phe Val Gln Asp Asn Val Asn Lys Asp
    2210            2215            2220

Ala Val Thr Asp Arg Leu Ala Ser Val Glu Thr Asp Met Pro Leu
    2225            2230            2235

Thr Leu Arg Gln His Arg Ile Ser Ala Thr Ser Ser Ser Glu Glu
    2240            2245            2250

Ser Ser Asn Lys Gly Gln Arg Gln Leu Thr Val Ser Pro His Gly
    2255            2260            2265

Tyr Leu Ser Asp Val Ala Ser Pro Pro Leu Leu Pro Ser Pro Phe
    2270            2275            2280

Gln Gln Ser Pro Ser Val Pro Leu Asn His Leu Pro Gly Met Pro
    2285            2290            2295

Asp Thr His Leu Gly Ile Gly His Leu Asn Val Ala Ala Lys Pro
    2300            2305            2310

Glu Met Ala Ala Leu Gly Gly Gly Gly Arg Leu Ala Phe Glu Thr
    2315            2320            2325

Gly Pro Pro Arg Leu Ser His Leu Pro Val Ala Ser Gly Thr Ser
    2330            2335            2340

Thr Val Leu Gly Ser Ser Ser Gly Gly Ala Leu Asn Phe Thr Val
    2345            2350            2355

Gly Gly Ser Thr Ser Leu Asn Gly Gln Cys Glu Trp Leu Ser Arg
    2360            2365            2370

Leu Gln Ser Gly Met Val Pro Asn Gln Tyr Asn Pro Leu Arg Gly
    2375            2380            2385

Ser Val Ala Pro Gly Pro Leu Ser Thr Gln Ala Pro Ser Leu Gln
    2390            2395            2400

His Gly Met Val Gly Pro Leu His Ser Ser Leu Ala Ala Ser Ala
    2405            2410            2415

Leu Ser Gln Met Met Ser Tyr Gln Gly Leu Pro Ser Thr Arg Leu
```

```
                2420                2425                2430
Ala Thr Gln Pro His Leu Val Gln Thr Gln Gln Val Gln Pro Gln
    2435                2440                2445

Asn Leu Gln Met Gln Gln Gln Asn Leu Gln Pro Ala Asn Ile Gln
    2450                2455                2460

Gln Gln Gln Ser Leu Gln Pro Pro Pro Pro Pro Gln Pro His
    2465                2470                2475

Leu Gly Val Ser Ser Ala Ala Ser Gly His Leu Gly Arg Ser Phe
    2480                2485                2490

Leu Ser Gly Glu Pro Ser Gln Ala Asp Val Gln Pro Leu Gly Pro
    2495                2500                2505

Ser Ser Leu Ala Val His Thr Ile Leu Pro Gln Glu Ser Pro Ala
    2510                2515                2520

Leu Pro Thr Ser Leu Pro Ser Ser Leu Val Pro Pro Val Thr Ala
    2525                2530                2535

Ala Gln Phe Leu Thr Pro Pro Ser Gln His Ser Tyr Ser Ser Pro
    2540                2545                2550

Val Asp Asn Thr Pro Ser His Gln Leu Gln Val Pro Glu His Pro
    2555                2560                2565

Phe Leu Thr Pro Ser Pro Glu Ser Pro Asp Gln Trp Ser Ser Ser
    2570                2575                2580

Ser Pro His Ser Asn Val Ser Asp Trp Ser Glu Gly Val Ser Ser
    2585                2590                2595

Pro Pro Thr Ser Met Gln Ser Gln Ile Ala Arg Ile Pro Glu Ala
    2600                2605                2610

Phe Lys
    2615

<210> SEQ ID NO 18
<211> LENGTH: 38
<212> TYPE: DNA
<213> ORGANISM: Artificial Sequence
<220> FEATURE:
<223> OTHER INFORMATION: syntehtic polynucleotide
<220> FEATURE:
<221> NAME/KEY: nick_site
<222> LOCATION: (31)..(32)

<400> SEQUENCE: 18
ccagtttctc gaagagaaac cggtaagtgc accctccc                              38

<210> SEQ ID NO 19
<211> LENGTH: 45
<212> TYPE: DNA
<213> ORGANISM: Artificial Sequence
<220> FEATURE:
<223> OTHER INFORMATION: synthetic polypeptide
<220> FEATURE:
<221> NAME/KEY: nick_site
<222> LOCATION: (28)..(29)

<400> SEQUENCE: 19
acgcgaacgg aacgttcgca taagtgcgcc cttacgggat ttaac                      45

<210> SEQ ID NO 20
<211> LENGTH: 130
<212> TYPE: PRT
<213> ORGANISM: Streptococcus pneumoniae

<400> SEQUENCE: 20
```

-continued

```
Met Ser Glu Lys Lys Glu Ile Val Lys Gly Arg Asp Trp Thr Phe Leu
1               5                   10                  15

Val Tyr Pro Glu Ser Ala Pro Glu Asn Trp Arg Thr Ile Leu Asp Glu
                20                  25                  30

Thr Phe Met Arg Trp Val Glu Ser Pro Leu His Asp Lys Asp Val Asn
            35                  40                  45

Ala Asp Gly Glu Ile Lys Lys Pro His Trp His Ile Leu Leu Ser Ser
50                  55                      60

Asp Gly Pro Ile Thr Gln Thr Ala Val Gln Lys Ile Ile Gly Pro Leu
65                      70                  75                  80

Asn Cys Pro Asn Ala Gln Lys Val Gly Ser Ala Lys Gly Leu Val Arg
                85                  90                  95

Tyr Met Val His Leu Asp Asn Pro Glu Lys Tyr Gln Tyr Ser Leu Asp
                100                 105                 110

Glu Ile Val Gly His Asn Gly Ala Asp Val Ala Ser Tyr Phe Glu Leu
                115                 120                 125

Thr Ala
    130

<210> SEQ ID NO 21
<211> LENGTH: 111
<212> TYPE: PRT
<213> ORGANISM: duck circovirus

<400> SEQUENCE: 21

Met Ala Lys Ser Gly Asn Tyr Ser Tyr Lys Arg Trp Val Phe Thr Ile
1               5                   10                  15

Asn Asn Pro Thr Phe Glu Asp Tyr Val His Val Leu Glu Phe Cys Thr
                20                  25                  30

Leu Asp Asn Cys Lys Phe Ala Ile Val Gly Glu Glu Lys Gly Ala Asn
            35                  40                  45

Gly Thr Pro His Leu Gln Gly Phe Leu Asn Leu Arg Ser Asn Ala Arg
        50                  55                      60

Ala Ala Ala Leu Glu Glu Ser Leu Gly Gly Arg Ala Trp Leu Ser Arg
65                  70                      75                  80

Ala Arg Gly Ser Asp Glu Asp Asn Glu Glu Tyr Cys Ala Lys Glu Ser
                85                  90                  95

Thr Tyr Leu Arg Val Gly Glu Pro Val Ser Lys Gly Arg Ser Ser
                100                 105                 110
```

POLYPEPTIDE TAGGING FUSIONS AND METHODS

CROSS-REFERENCE TO RELATED APPLICATION

This application claims priority to U.S. Provisional Patent Application No. 62/163,506, filed May 19, 2015, which is incorporated herein by reference.

SEQUENCE LISTING

This application contains a Sequence Listing electronically submitted via EFS-Web to the United States Patent and Trademark Office as an ASCII text file entitled "11004920101_SequenceListing_ST25.txt" having a size of 65 kilobytes and created on May 19, 2016. The information contained in the Sequence Listing is incorporated by reference herein.

SUMMARY

This disclosure describes, in one aspect, a fusion polypeptide. Generally, the fusion polypeptide includes at least a portion of a polypeptide of interest and at least a functional portion of an HUH polypeptide. Typically, the functional portion of the HUH polypeptide includes at least a portion of a Rep and/or relaxase domain. Generally, the Rep and/or relaxase domain includes at least one catalytic polar amino acid residue and at least one metal-coordinating amino acid residue.

In some embodiments, the fusion polypeptide can further include a detectable label.

In another aspect, this disclosure describes a molecular complex. Generally, the molecular complex includes an oligonucleotide and a fusion polypeptide, as summarized above, that specifically binds to the oligonucleotide.

In some embodiments, the oligonucleotide can include DNA such as, for example, DNA origami. In other embodiments, the oligonucleotide can include RNA such as, for example, RNA origami.

In another aspect, this disclosure describes a composition that includes an oligonucleotide and a fusion polypeptide, as summarized above, that specifically binds to the oligonucleotide.

In some embodiments, the composition can include a second oligonucleotide and a second fusion polypeptide, as summarized above, that specifically binds to the second oligonucleotide, In another aspect, this disclosure describes methods that involve the fusion polypeptide, molecular complex, and/or composition as summarized above.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

The patent or application file contains at least one drawing or photograph executed in color. Copies of this patent or patent application publication with color drawing(s) or photographs(s) will be provided by the Office upon request and payment of the necessary fee.

DETAILED DESCRIPTION OF ILLUSTRATIVE EMBODIMENTS

Figure 1:
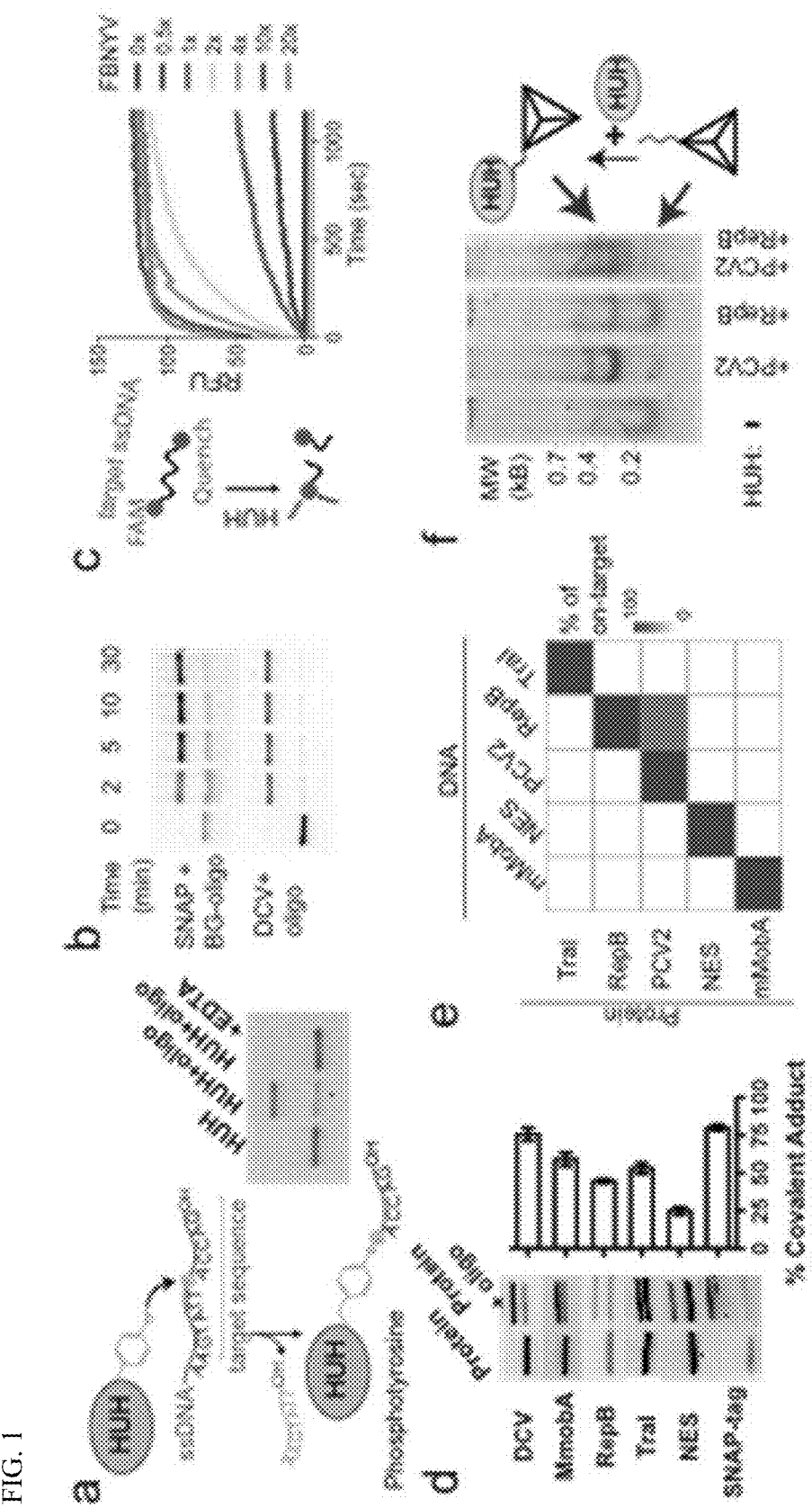
FIG. 1: In vitro investigations of HUH-tags. (A) Schematic illustration of reaction chemistry showing catalytic tyrosine in HUH endonuclease nicking ssDNA and forming a covalent phosphotyrosine adduct. SDS-PAGE showing formation of covalent adduct between DCV and target on oligonucleotide in the presence of $Mn^{2+}$ and EDTA. (B) Time course of covalent adduct formation of the HUH-tag DCV and the SNAP-tag with four-fold excess of target DNA using SDS-PAGE. (C) De-quenching assays monitor nicking of an HUH-target oligo flanked by donor and quencher dyes, which leads to appearance of fluorescence. Here, varying concentrations of fava bean necrotic yellows virus (FBNYV) HUH-tag (62.5 nM to 2500 nM) were added to 125 nM quenched PCV-target oligo, and FAM fluorescence monitored as a function of time using a fluorescence plate reader. (D) Comparison of covalent adducts formed by reaction of five HUH-tags with 10-fold excess of respective target oligos for 15 minutes at 37° C. on SDS-PAGE. Yield of covalent adduct was calculated for three replicates using ImageJ gel-band quantitation functions. Error bars report standard error. (E) Heat map of DNA target sequence preferences of HUH-tags. Indicated HUH proteins were incubated individually with a 10-fold excess of preferred oligonucleotide on sequences for each HUH protein; the reaction products were analyzed by SDS-PAGE and quantified. (F) Proteins were incubated in 10-fold excess with a DNA tetrahedron bearing target ssDNA on its corners; the reaction products were analyzed by 5% TBE-PAGE supplemented with 0.1% SDS and stained with SYBR Gold (Invitrogen, Thermo Fisher Scientific, Inc., Waltham, Mass.).

The ability to covalently attach DNA to proteins has broad applications in, for example, DNA nanotechnology, cellular imaging, and/or targeted nucleotide delivery. DNA is highly programmable, easy and cost-effective to manipulate, and can be engineered to include various useful modifications such as, for example, a fluorophore, a reactive chemical moiety, and/or a photocrosslinker. Current strategies for conjugating DNA to a protein involve using a thiol and/or an amine moiety encoded in oligonucleotides to couple to proteins, but these strategies can lack specificity. Another conventional method involves enzymatic ligation of a protein fusion tag such as a SNAP tag (New England Biolabs, Inc., Ipswich, Mass.) or a HALOTAG (Promega, Madison, Wis.) tags) to a modified DNA base. However, these require modified oligonucleotides to attach the target bases, along with purification and verification of the strands, and even then are still limited to two or three orthogonal attachment sites.

This disclosure describes the construction and use of a group of proteins that recognize a specific sequence of unmodified DNA and form stable covalent bonds between the protein and the unmodified DNA. The proteins include HUH endonuclease domains. HUH endonuclease domains are present in hundreds of viral replication proteins, at least 20 relaxases, and many transposases. The HUH proteins are so named because of a catalytic motif that most commonly involves two histidines and a third amino acid that is usually a polar amino acid. The amino acids in the catalytic motif coordinate a metal. HUH proteins represent a group of proteins that include, for example, virus proteins and bacterial relaxases. In many cases, an HUH protein contains an N-terminal "Rep" or "relaxase" domain that contains the HUH catalytic motif, including a catalytic tyrosine as the polar amino acid residue. A HUH protein often includes at least one domain in addition to the Rep/relaxase domain such as, for example, a helicase domain). The HUH-based fusion polypeptides described herein include at least a functional portion of the HUH domain—i.e., the metal coordinating amino acid residues (typically histidine residues) and the catalytic tyrosine residue.

The HUH endonuclease-based fusion-tag strategy described herein can covalently link DNA to a protein of interest by exploiting the native covalent DNA linking character of the HUH endonucleases. The HUH endonucleases possess a small "nicking domain" that in isolation can bind a specific single-stranded DNA sequence, nick the DNA sequence using a transesterification mechanism similar to that of topoisomerases, and subsequently form a covalent phosphotyrosine link between the protein and the 5' end of the DNA strand. (FIG. 1A) This nicking domain is often found in series with other protein domains—e.g., a helicase domain, a primase domain, and/or a multimerization domain. The nicking activity of several HUH endonucleases has been characterized biochemically and structurally. The catalysis often involves coordinating a magnesium ion, a nickel ion, or a manganese ion in the active site by two conserved histidines and a polar residue 'U' that form the so-called "HUH motif" (see, e.g., SEQ ID NOS:3-6 and 8), although the HUH motif may possess only one histidine residue (see, e.g., SEQ ID NOS:2 and 7). Exemplary metal-coordinating histidine residues are found at, for example, residue 57 of SEQ ID NO:2, residue 90 and residue 92 of SEQ ID NO:3, residue 120 and residue 122 of SEQ ID NO:4, residue 157 and residue 159 of SEQ ID NO:5, residue 55 and residue 57 of SEQ ID NO:6, residue 41 of SEQ ID NO:7, residue 130 and residue 132 of SEQ ID NO:8, residue 161 and residue 163 of SEQ ID NO:9, residue 55 and residue 57 of SEQ ID NO:10, residue 57 and residue 59 of SEQ ID NO:20, and residue 52 of SEQ ID NO:21.

While described herein in the context of exemplary embodiments in which the polar catalytic amino acid residue is a tyrosine residue, a HUH polypeptide can include any suitable catalytic polar amino acid residue such as, for example, a serine residue, a threonine residue, or a cysteine residue. Exemplary polar catalytic amino acid residues are found at, for example, residue 96 of SEQ ID NO:2, residue 128 of SEQ ID NO:3, residue 25 of SEQ ID NO:4, residue 16 of SEQ ID NO:5, residue 99 of SEQ ID NO:6, residue 79 of SEQ ID NO:7, residue 24 of SEQ ID NO:8, residue 26 of SEQ ID NO:9, residue 101 of SEQ ID NO:10, residue 97 of SEQ ID NO:20, and residue 91 of SEQ ID NO:21.

The nicking domains of HUH endonucleases can range in size from 90-300 amino acids. Moreover, there are many examples of HUH endonucleases in nature, each with its own specific target sequence. Therefore, a library of HUH fusion-tagged proteins, each protein of interest with a unique HUH tag, can allow one to specifically label many proteins in the same reaction mixture at the same time. A panel of exemplary HUH-endonuclease is provided in Table 1.

TABLE 1

Properties of exemplary HUH-tags.

| HUH-tag | Full name | Pdb ID | MW (kDa) | pI | Ori sequence<sup>&</sup> |
|---|---|---|---|---|---|
| PCV2* (SEQ ID NO: 2) | Porcine circovirus 2 | 2HW0 | 13.4 | 9.5 | aagtatt/accagaaa (SEQ ID NO: 12) |
| DCV (SEQ ID NO: 21) | Duck circovirus | | 13.4 | 5.4 | |
| FBNYV^ (SEQ ID NO: 7) | Faba bean necrosis yellow virus | 2HWT | 11.3 | 8.6 | |
| RepB# (SEQ ID NO: 6) | Replication protein RepB *Streptococcus agalactiae* | 3DKY | 15.2 | 9.4 | tgcttccgtactacg/accccca (SEQ ID NO: 15) |
| RepBm (SEQ ID NO: 20) | RepB *Fructobacillus tropaeoli* | | 14.7 | 5.5 | |
| TraI+ (SEQ ID NO: 5) | Conjugation protein TraI *E. coli* | 1P4D | 36.4 | 5.6 | tttgcgtggggtgt/ggtgcttt (SEQ ID NO: 13) |
| mMobA° (SEQ ID NO: 4) | Mobilization protein A *E. coli* | 2NS6 | 20.9 | 6.3 | ccagtttctcgaagaga aaccggtaagtgca/ ccctccc (SEQ ID NO: 18) |
| NES@ (SEQ ID NO: 8) | Nicking enzyme *Staphylococcus aureus* | 4HT4 | 25.9 | 6.7 | acgcgaacggaacgttc gcataagtgcg/ccctt acgggatttaac (SEQ ID NO: 19) |

<sup>&</sup>slash (/) denotes site of cleavage by endonuclease
*Vega-Rocha et al., J. Mol. Biol. 367, 473-487 (2007).
^Vega-Rocha et al., Biochemistry 46, 6201-6212 (2007).
Boer et al., EMBO J. 28, 1666-1678 (2009).
+Datta et al., Structure/Folding and Design 11, 1369-1379 (2003).
°Monzingo et al., J. Mol. Biol. 366, 165-178 (2007).
@Edwards et al., Proceedings of the National Academy of Sciences 110, 2804-2809 (2013).

TABLE 2

| HUH polypeptide | SEQ ID NO: | Function Fragment |
|---|---|---|
| PCV2 | SEQ ID NO: 2 | Amino acids 16-99, with or without deletion within amino acids 46-55 |
| mMobA | SEQ ID NO: 4 | Amino acids 6-126 |
| RepB | SEQ ID NO: 6 | Amino acids 6-101 |
| FBNYV | SEQ ID NO: 7 | Amino acids 7-94 |
| RepBm | SEQ ID NO: 20 | Amino acids 12-98 |
| DCV | SEQ ID NO: 21 | Amino acids 11-101 |

This disclosure describes adapting the HUH catalytic motif for protein tagging in vitro and in cells. The tags robustly form covalent complexes with DNA oligonucleotides in vitro. The catalytic residue of an HUH endonuclease can be a tyrosine that forms a phosphotyrosine ester with the target DNA.

As noted above, the HUH catalytic motif includes the metal-coordinating histidine residue or residues and a catalytic polar amino acid residue. Thus, a fusion polypeptide can include any functional fragment of an HUH polypeptide. A functional fragment of an HUH polypeptide will include the metal-coordinating histidine residue or residues and the polar amino acid residue and sufficient additional amino acids to allow the fragment to possess DNA nicking activity. Exemplary suitable fragments of exemplary HUH polypeptides are provided in Table 2.

In addition to or as an alternative to the fragments listed in Table 2, an HUH polypeptide can include one or more amino acid sequence modifications compared to the listed amino acid sequences. In certain cases, the amino acid sequence modification can include a deletion of one or more amino acid residues such as, for example, deletion of one or more of amino acids 46-55 of SEQ ID NO:2. In other cases, an amino acid modification can include a conservative amino acid substitution. A conservative substitution for an amino acid in a reference amino acid sequence may be selected from other members of the class to which the amino acid belongs. For example, it is well-known in the art of protein biochemistry that an amino acid belonging to a grouping of amino acids having a particular size or characteristic (such as charge, hydrophobicity, or hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Conservative substitutions include, for example, Lys for Arg or Arg for Lys to maintain a positive charge, Glu for Asp or Asp for Glu to maintain a negative charge, Ser for Thr so that a free —OH is maintained, and Gln for Asn to maintain a free —NH$_2$. Likewise, biologically active analogs of a polypeptide containing deletions or additions of one or more contiguous or noncontiguous amino acids that do not eliminate a functional activity of the polypeptide are also contemplated.

An HUH polypeptide also can be designed to provide additional sequences, such as, for example, an addition of one or more amino acid residues added C-terminal or N-terminal amino acids that would facilitate purification by trapping on columns or use of antibodies. Such tags include, for example, histidine-rich tags (see, e.g., SEQ ID NO:16 and SEQ ID NO:17) that allow purification of polypeptides on nickel columns. Such gene modification techniques and alternative suitable additional sequences are well known in the molecular biology arts.

HUH-endonucleases were expressed in E. coli in fusion with an N-terminal His$_6$-SUMO domain, and purified them using affinity chromatography and size exclusion chromatography. Reacting recombinant SUMO-DCV with a single stranded oligo bearing its target sequence in the presence of Mn$^{2+}$ results in formation of a characteristic covalent adduct, which runs slower on SDS-PAGE (FIG. 1A). Treating the protein first with EDTA results in no covalent adduct.

To compare the formation of the covalent HUH adduct formation with the conventional SNAP-tag, the benzylguanine SNAP substrate was chemically linked to a DNA oligo to result in a substrate that would produce a shift on SDS-PAGE analogous to the HUH-tag. The recombinant SNAP-tag and SUMO-DCV were reacted with a four-fold excess of their respective target oligos and analyzed the reaction by SDS-PAGE (FIG. 1B). Both reactions robustly form covalent adducts, with the DCV reaction achieving maximal yield in under five minutes, compared to 10 minutes for the SNAP-tag.

HUH-endonuclease activity was monitored using an oligo containing a donor-fluorophore and quencher flanking the HUH nicking site (FIG. 1C). Nicking results in de-quenching of the fluorophore, allowing activity to be monitored by fluorescence. Reacting such an oligo with varying concentrations of SUMO-FBNYV shows efficient cleavage even at 1:1 HUH:oligo and achieving maximal cleavage rates at ~4×HUH protein (FIG. 1C).

An advantage of using HUH-tag fusion partners is that there are several classes of HUH-endonucleases with divergent structures, DNA recognition motifs, and/or functions. This characteristic allows which allows one to design a panel HUH-based fusion polypeptides, each of which binds to a distinct sequences of ssDNA, for use in, for example, multiplexed labeling of multiple species in a single reaction. Five SUMO-HUH fusions were tested for their ability to form covalent adducts. FIG. 1D shows that all SUMO-HUH fusions, although not engineered for optimal function, resulted in covalent adduct formation, with yields ranging from 25-80%. The most efficient HUH-tag PCV2 (and the functionally-related tags DCV and FBNYV derived from viral proteins involved in rolling circle replication) has activity similar to the heavily engineered SNAP protein.

The sequence specificity of these tags were tested by reacting each HUH-protein with a 10-fold excess of each target DNA, and quantitated the formation of covalent adducts. FIG. 1E shows that the HUH-tags generally displayed stringent sequence specificity.

Figure 2:
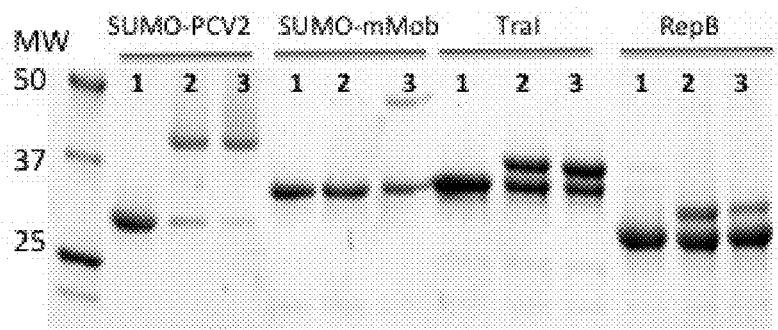
FIG. 2. SDS-PAGE gel of four purified HUH proteins forming covalent complexes with their target sequences using Stain-Free gel imaging. The proteins (without DNA in columns #1) were mixed with an approximately three-fold excess of DNA in the presence of 1 mM $MnCl_2/MgCl_2$ and reacted at 37° C. for one minute (columns #2) or 20 minutes (columns #3).
Figure 3:
FIG. 3: SDS-PAGE gel of time course of reaction of SUMO-PCV2 (~30 kDa) with a Cy5-labeled PCV2 target oligonucleotide (left half). The right half of the gel shows the addition of SUMO-GeneA (~60 kDa) and a FAM labeled GeneA target oligonucleotide. The top of the gel shows detection of the Cy5 (red) and FAM (green) oligonucleotide using a TYPHOON imaging system (GE Healthcare Bio-Sciences, Pittsburgh, Pa.). The bottom is the same gel stained with Coomassie blue.

FIG. 2 shows an SDS-PAGE gel showing covalent complexes formed by several exemplary HUH fusions using HUH tags listed in Table 1. This figure shows the reaction of recombinantly expressed HUH proteins fused to a SUMO tag with their target DNAs. The reaction time is extremely fast. FIG. 3 shows an SDS-PAGE gel showing time course of reaction of PCV2 and GeneA with their target oligonucleotides. Product is observed after a reaction time of only five minutes. Adding GeneA and its oligonucleotide (green) to PCV and its oligonucleotide (red) shows reaction of target oligonucleotide with its correct protein and no cross-reactivity.

Figure 4:
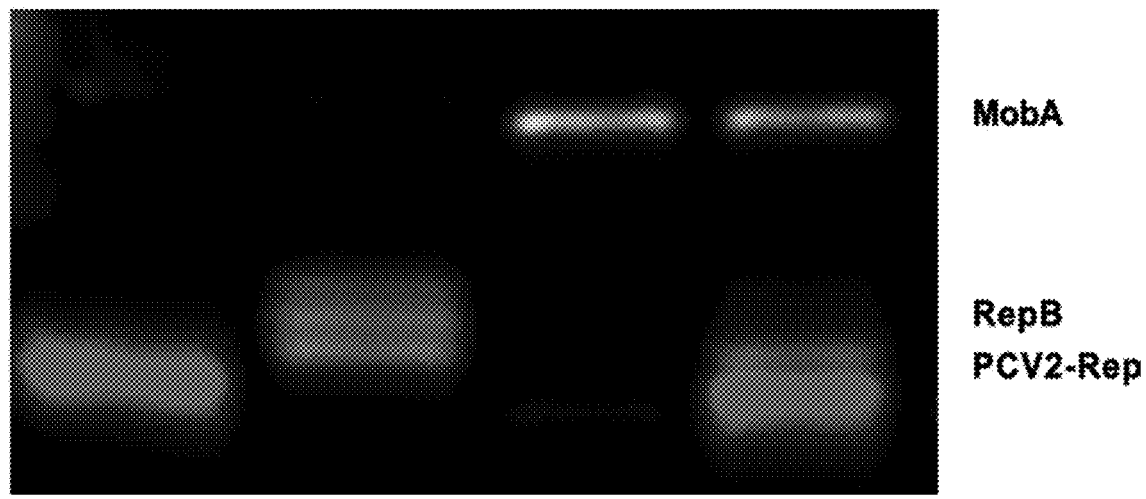
FIG. 4: SDS-PAGE and TYPHOON imaging detection of three purified HUH proteins-PCV2 (lane1), RepB (lane2), and miniMob (lane3) reacted with target oligonucleotides: pcv2-cy5 (red), repb-FAM (green), and miniMob-Cy3 (yellow). The first three lanes have a single target oligonucleotide reacted with all three target HUH proteins. The last lane shows the reaction of all three proteins with all three target oligonucleotides. 1 μM purified protein was reacted with 5 μM labeled target DNA for 30 minutes at 37° C. Reactions were separated by SDS-PAGE and imaged using a TYPHOON FLA 9500 (GE Healthcare Bio-Sciences, Pittsburgh, Pa.).

The HUH endonuclease-based protein tags described herein allow one to orthogonally label proteins in cells. FIG. 4 shows an SDS-PAGE gel showing orthogonality of three HUH proteins. This gel shows that reaction of PCV2, RepB, and miniMob with a mixture of the three target oligonucleotides labeled red, green, and yellow results in only one product in the first three lanes and three products when all three proteins and all three oligonucleotides are present. At least five HUH endonuclease-based tags exhibit orthogonal labeling.

Figure 5:
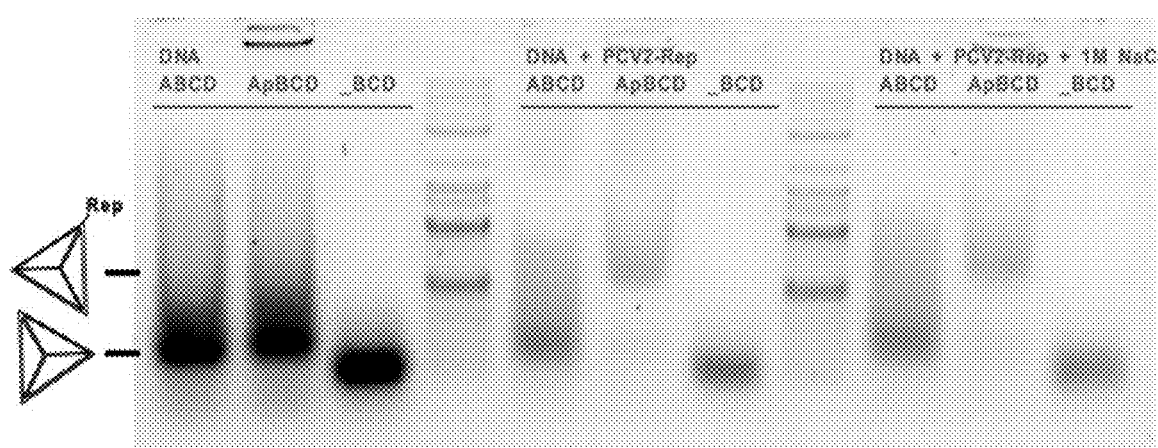
FIG. 5: Agarose gel showing detection of HUH protein binding to a DNA origami structure. ABCD are the four sides of the tetrahedral DNA. Ap is sideA containing the PCV2 target sequence. DNA tetrahedra were assembled by combining four strands at 10 μM concentration each in TM buffer (10 mM Tris-HCl, pH 8.0, 10 mM $MgCl_2$) and heating to 95° C. for five minutes followed by rapid cooling to 4° C. Assembled structures were reacted with equimolar purified PCV2-Rep at 1 μM concentration in 20 mM Tris-HCl, pH 8.0, 200 mM NaCl, and 10 mM $MgCl_2$ for 30 minutes at 37° C. 5 M NaCl was added post-reaction to dissociate nonspecific protein-DNA interactions. 10 μL of each reaction were separated on 1.5% agarose at 7V/cm in TAE+10 mM $MgCl_2$ for 60 minutes; unreacted structures were run at 10 μM concentration. BCD indicates a structure where A strand is omitted (negative control).

The HUH endonuclease-based protein tags described herein allow attachment of proteins to DNA and/or RNA origami. FIG. 1F shows a shift of the tetrahedron DNA in the presence of PCV2 and RepB. A similar shift is observed using mMobA on a larger six-helix bundle nanostructure. FIG. 5 shows additional data involving reaction between a tetrahedral DNA origami structure and the PCV2 HUH protein. A common DNA origami structure was constructed out of four long oligonucleotides, folded, and characterized on an agarose gel. When one oligonucleotide was replaced with an oligonucleotide containing the PCV2 target sequence, the gel noticeably shifts with the addition of the PCV2 protein. These data show the utility of HUH tagging for synthetic biology applications involving assembly of proteins in specific orientations and stoichiometry on DNA origami structures. This application of the HUH tagging can be extended to mammalian cell lysates and/or bacterial cell lysates.

The attachment of proteins to DNA or RNA origami allows one to use the HUH tagging for synthetic biology applications—e.g., synthesizing drugs or metabolic products (e.g., biofuels) and/or assembly of molecular machines.

Figure 6:
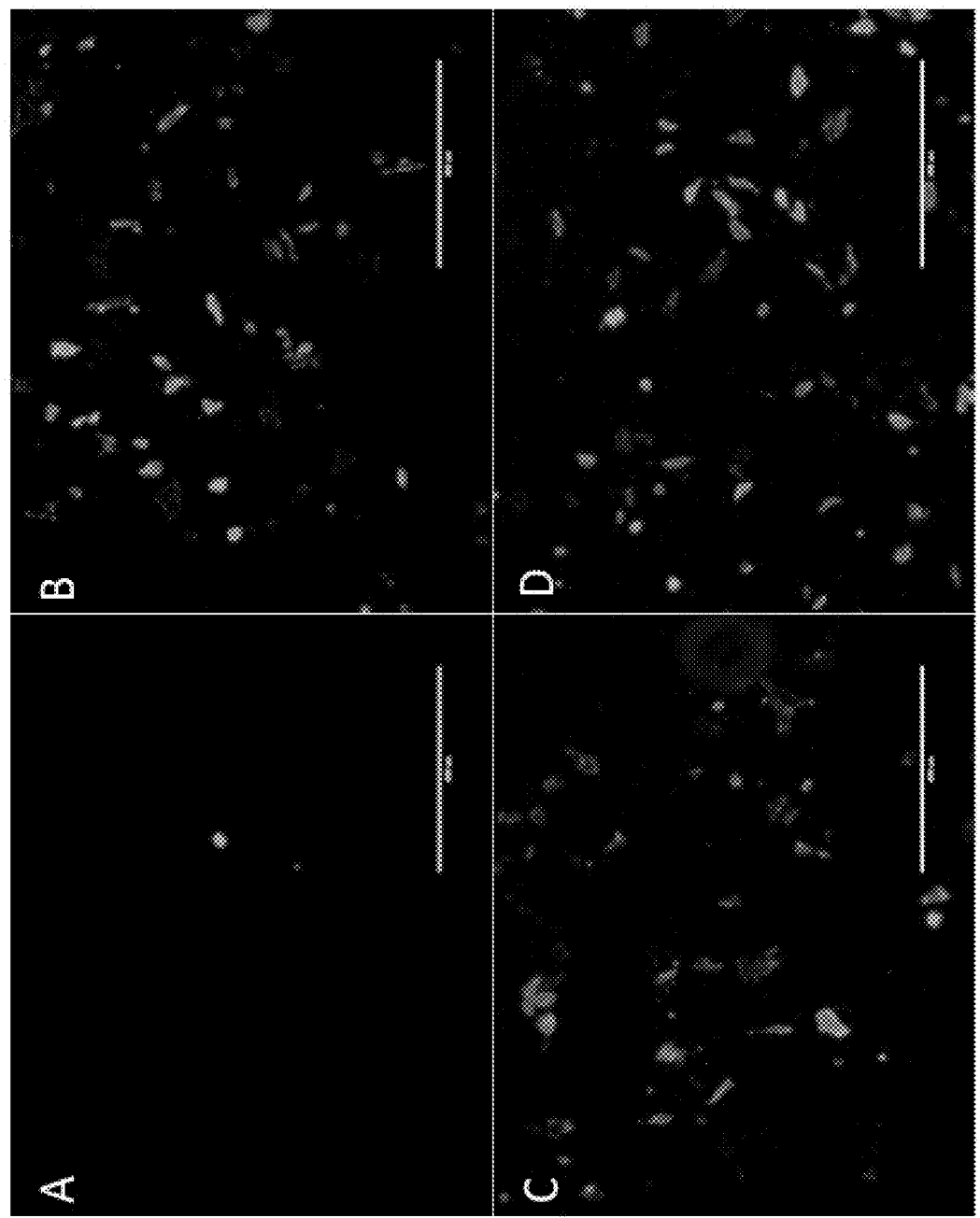
FIG. 6: N-terminal fusions of mMobA and TraI36 do not alter cell surface expression of transmembrane Notch receptors. U2OS cells were transiently transfected with empty vector (A), FLAG-Notch1 (B), FLAG-mMobA-Notch1 (C) or FLAG-TraI36-Notch1 (D) in clear bottom 96-well plates. 24 hours later, cells were stained for the FLAG epitope tag using APC conjugated anti-FLAG antibody or 30 minutes and imaged using the EVOS FL-Auto widefield fluorescence microscope (Life Technologies Corp., Carlsbad, Calif.).
Figure 7:
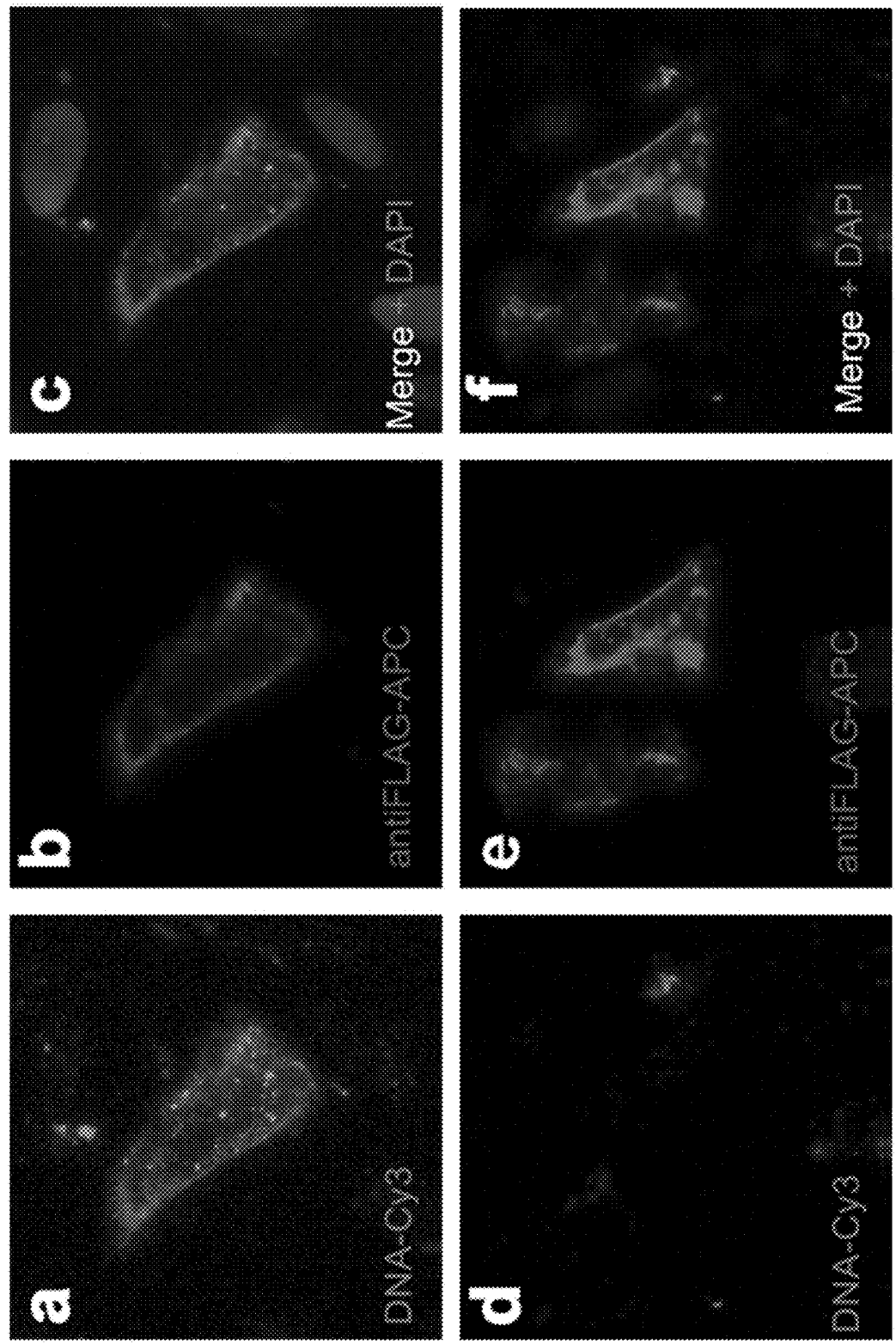
FIG. 7: Live cell imaging of Notch receptors on the cell surface using the mMobA HUH fusion. A construct FLAG-mMobA-Notch1-Gal4 in pcDNA5 (A-C) or FLAG-TraI36-Notch1-Gal4 (D-F) was transiently transfected in U2OS cells in clear bottom 96-well plates (Corning, Inc., Corning, N.Y.). 24 hours post-transfection, cells were labeled with 500 nM mMobA target oligonucleotide conjugated to Cy3 (green) in DMEM containing 10% FBS. The reaction mix also contained 0.5 mM $MnCl_2$ and $MgCl_2$, 0.1 mM salmon sperm DNA, 5 μg/ml APC conjugated anti-FLAG antibody (red) and Hoechst stain for 20 minutes at 37° C. The cells were washed three times with PBS, and fluorescence imaging media was added. Cells were imaged using an EVOS FL-Auto widefield fluorescence microscope (Life Technologies Corp., Carlsbad, Calif.).

The HUH endonuclease-based protein tags can be used in cellular imaging applications. FIG. 6 shows a comparison of cell surface expression of wild-type Notch1 receptors containing a N-terminal FLAG tag with N-terminal HUH fusions mMobA and TraI136 (retaining FLAG tag for comparison). U2OS cells were transiently transfected with constructs, and stained with APC conjugated anti-FLAG antibody after 24 hours. Fusion proteins exhibited similar surface expression to the wildtype Notch molecule. FIG. 7 shows live cell surface labeling of HUH-tagged Notch receptor. Here wild-type FLAG-tagged Notch or the same molecule containing an N-terminal mMobA fusion was transiently transfected in U2OS cells. Labeling was performed after 24 hours in media supplemented with 0.5 mM MgCl$_2$ and MnCl$_2$ using 500 nM Cy3-conjugated mMob target oligonucleotide (green). The APC-anti-FLAG antibody (red) and nuclear Hoescht stain (blue) were also included. Here we see that while both wild-type and mMobA Notch stain with the APC-FLAG antibody (red), only the mMobA Notch is stained with the mMobA target oligonucleotide (green). We have evidence of labeling inside cells using fixed cells and are working on ways of delivering the oligonucleotides in for live intracellular labeling (transfection, origami structure, gold nanoparticles). Since this labeling is covalent, events can be followed for long times.

Figure 8:
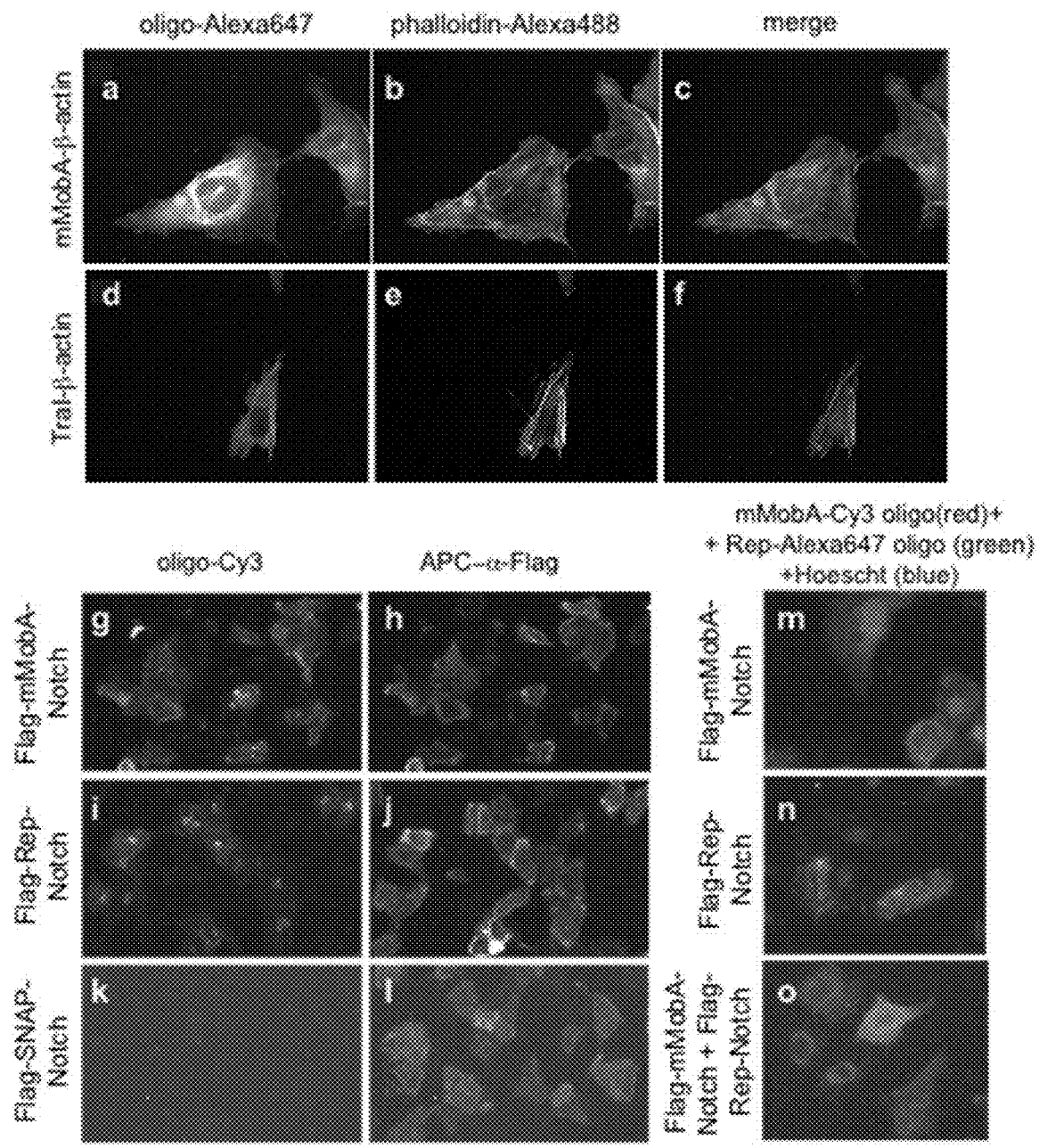
FIG. 8. Use of HUH-tags in cellular imaging. All images were collected on an EVOS-FL-Auto widefield fluorescence microscope (Life Technologies Corp., Carlsbad, Calif.) using standard Plan Fluorite objectives. (A-F) Intracellular imaging. U2OS cells were transfected with vectors expressing HUH-actin fusion proteins, fixed after 24 hours, and stained using Alexa647-labeled target oligonucleotides. Cellular actin filaments were stained with Alexa488-phalloidin and DNA stained with DAPI. (G-L) Cell-surface imaging. Truncated Notch receptors were encoded with a Flag-epitope followed by an HUH or SNAP tag at the N-terminus and transfected into U2OS cells in clear bottom 96-well plates. Cells were labeled with Cy3-oligos bearing the HUH-target sequence and an APC-conjugated Flag antibody for 20 minutes. After washing they were stained with Hoechst stain and imaged live. (M-O) Orthogonal labeling of two HUH-tags on cell-surface. Cells containing mMob-Notch (M), Rep-Notch (N) or co-cultured cells (O) were stained with a mixture of target oligos bearing different fluorophores along with Hoechst nuclear stain.

FIG. 8 shows data confirming the in vivo utility of the HUH-fusion tags. To assess the use of HUH-tags for labeling in fixed cells and effects on cellular localization, TraI or mMobA was fused to the N-terminus of human β-actin and expressed in U2OS cells. Labeling the fixed TraI/mMobA-β-actin cells with 3'-Alexa647 ori oligos showed labeling of both actin filaments and cytoplasmic actin (FIGS. 8A and 8D). Counterstaining with phalloidin488 showed that the fusion protein was efficiently incorporated into actin filaments (FIGS. 8B and 8E). Control cells, transfected with EGFP-β-actin and mock labeled with either fluorescent on showed no fluorescence in the far-red region, indicating that non-specific sticking of the DNA is not responsible for labeling.

HUH-tags are compatible with live-cell imaging. N-terminal fusions of mMobA or RepBm exhibited good cell-surface trafficking in U2OS cells compared to a SNAP-fused Notch receptor, as shown by labeling the FLAG-epitope tag with an APC conjugated antibody (FIGS. 8H, 8J, and 8L). Treating the cells expressing HUH-fusion tags with 3'Cy3-oligos bearing respective target sequence (FIGS. 8G, 8I, and 8K) only results in labeling of cells that also show FLAG staining, showing that non-specific sticking of DNA is not responsible for labeling. Optimal labeling occurred using 200 nM fluorescent target oligo in standard serum-containing media, supplemented with $Mn^{2+}$ and salmon sperm DNA, for 15-20 minutes at 37° C. To demonstrate orthogonal cell-surface labeling, cells transfected with the RepBm-Notch fusion were co-cultured with cells transfected with the mMob-Notch fusion, then treated with a mixture of 3'Cy3-mMob and 3'Alexa647-Rep target oligos (FIG. 8M-O). Cells expressing single receptors only show labeling with one color, while both fluorophores are observed when both cell types are present. mMobA and RepBm fusions of full-length Notch receptors signal normally when co-cultured with ligands in a transcriptional luciferase reporter assay and can also be labeled with fluorophore-conjugated oligos, further suggesting that the HUH-tags do not disrupt protein function when used as fusion partners in mammalian cells.

Thus, this disclosure describes the design, construction, and use of HUH-fusion polypeptides. In certain applications, the HUH fusion polypeptides can be attached to DNA origami structures. In other applications, the HUH fusion polypeptides can provide fluorescent labeling of cell-surface receptors in live cells. In still other applications, an HUH-tag can be fused to a nanobody or single chain antibody to allow specific delivery of DNA into cells. In yet another application, an HUH-tag may be a delivery agent—e.g., the charged nature of PCV2 allows it to cross the cell membrane even in the absence of cationic lipids.

SEQ ID NO:16 and SEQ ID NO:17 represent exemplary fusion tags in which Notch 1-Gal4 is fused to a portion of an HUH endonuclease. SEQ ID NO:16 reflects an HUH fusion tag that includes a portion of mMobA ("minimal MobA"), while SEQ ID NO:17 reflects an HUH fusion tag that includes a portion of TraI36. Each exemplary HUH-tagged fusion protein includes a functional portion of the HUH endonuclease Rep domain—i.e., the metal-coordinating amino acid residues and the catalytic tyrosine residue.

The HUH-tagged mMobA fusion protein specifically binds the oligonucleotide sequence:

(SEQ ID NO: 14)
5'-CCAGTTTCTCGAAGAGAAACCGGTAAATGCG*CCCT-3' where the asterisk denotes the HUH endonuclease nick site. The HUH-tagged TraI36 fusion protein specifically binds the oligonucleotide sequence:

(SEQ ID NO: 13)
5'-TTTGCGTGGGGTGT*GGTGCTTT-3' where, again, the asterisk denotes the HUH endonuclease nick site.

Conventional protein tags that employ small protein modules based on DNA repair enzymes that form a covalent bond with DNA must do so through a modified DNA base. In contrast, the HUH tags described herein recognize a specific sequence of standard nucleotides rather than modified bases. The conventional protein tags also use a catalytic cysteine, which can be prone to deactivation by oxidation. In contrast, as discussed above, HUH endonucleases use a catalytic tyrosine residue, which is less vulnerable to deactivation than cysteine. Moreover, more than twenty HUH polypeptides are known, which allows a person more possibilities for orthogonal labeling and/or assembling molecular machines. Also, many of the HUH proteins are smaller (100 amino acids) than conventional (e.g., SNAP/CLIP (New England Biolabs, Inc., Ipswich, Mass.) or HALOTAG (Promega, Madison, Wis.)) protein tags, so they may be less disruptive to protein function than the larger conventional tags, which can be 200-300 amino acids in size.

Equivalent RNA nuclease enzymes may be used to attach proteins to RNA origami scaffolds. Both HUH endonucleases and equivalent RNA enzymes may be engineered to bind any DNA sequence or to be smaller to further enhance downstream applications.

Other cellular imaging applications can involve barcoding of cells with DNA, superresolution imaging such as, for example, DNA-PAINT (Jungmann et al., 2012, *Nat Methods* 11(32):313-318), which involves transient binding of a fluorophore-conjugated DNA oligonucleotide to an oligonucleotide on the protein of interest.

Another application of HUH tagging includes, for example, DNA-based drug delivery. For example, one can fuse an HUH tag to a recombinant antibody in order to deliver nucleic acids to cells that are targeted by the antibody.

Thus, the HUH endonuclease catalytic motif is useful as a fusion tag. HUH tags can provide efficient formation of covalent bonds, require only a specific sequence of DNA rather than chemically-modified bases, and/or allow for multiplexed labeling in a single reaction. HUH tag-target DNA reaction is compatible with a variety of in vitro conditions, standard cell-culture media, cellular lysates, and with fixing cells. HUH-tags expand the protein-labeling capabilities for in vitro applications such as DNA nanotechnology, where one can immobilize multiple HUH-tagged proteins expressed in the same cell lysate directly onto a DNA origami structure, without intermediate purification steps. HUH-tags also can be used in the context of DNA-based in vivo cellular imaging applications such as proximity-ligation assays or DNA-PAINT. Designing the target sequence for a particular HUH-tag can enhance yield of covalent complex and/or specificity. Moreover, an HUH-endonuclease may be designed—e.g., by amino acid mutation—to alter DNA sequence specificity.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Materials: Oligonucleotides were ordered from Integrated DNA Technologies, Inc. (Coralville, Iowa). HUH sequences were all purchased as codon-optimized oligonucleotides from Life Technologies, Inc. (Thermo Fisher Scientific, Waltham, Mass.) or Integrated DNA Technologies, Inc.

Cloning of Constructs:

All constructs for *E. coli* expression were cloned into a pET15b (Novagen, EMD Millipore, Billerica, Mass.) based plasmid containing an N-terminal His6 tag followed by a SUMO tag. Constructs were inserted into the vector cut with BamH1 and Xho1 using INFUSION cloning (Clontech Laboratories, Inc., Mountain View, Calif.) or standard methods (New England Biolabs, Inc., Ipswich, Mass.). Mammalian constructs were prepared by inserting oligonucleotides into an existing FLAG-Notch1-Gal4 sequence in pCDNA5 cut with Kpn1 using INFUSION cloning or into pCDNA3.

Expression and Purification of SUMO-HUH Constructs.

Sequence confirmed clones were transformed into BL21-(DE3) cells. Seven ml overnight cultures were grown in LB media containing 100 µg/ml ampicillin and seeded 1:1000 into 500 ml or 1 L of LB containing ampicillin. Bacteria were grown at 37° C. to an $OD_{600}$ of 0.6-0.8 and induced with 0.4 mM IPTG overnight at 18° C. Expression can also be performed at 37° C. for three hours. Cells were pelleted at 2000-4000×g for 10-20 minutes. Pellets were then lysed by sonication in the presence of EDTA-free protease inhibitor tablets (Roche Diagnostics Corp., Indianapolis, Ind.) in lysis buffer. Soluble supernatant was collected after spinning at 25000×g for 60 minutes. 2-3 ml of Ni-NTA beads were added to lysate and Ni-NTA purification was performed using standard protocols with the addition of a wash using 1 M NaCl. Protein was eluted in 250 mM imidazole, concentrated, and purified using size exclusion chromatography. Protein was concentrated and frozen at −80° C. for later use.

Cell-Surface Expression.

Sequence confirmed clones were maxi-prepped and transiently transfected into U2OS cells using LIPOFECTAMINE 3000 (Life Technologies, Thermo Fisher Scientific, Inc., Waltham, Mass.). For 96-well plate transfections, transfections involved 0.2 µl LIPOFECTAMINE in 5 µl OPTI-MEM (Life Technologies, Thermo Fisher Scientific, Inc., Waltham, Mass.) and 0.2 µl P3000, 0.1 µg DNA plasmid in 5 µl OPTI-MEM per well. Cells were plated on the liposomes at the same time as the transfection so that total volume in each well was 70 µl. An equal volume of full media (DMEM plus 10% FBS) was added 3-6 hours post-transfection. After 24 hours, cells were labeled with 50 µl Cy3-mMobA oligonucleotide in full media supplemented with 0.1 mg/ml salmon sperm DNA, 0.5 mM $MgCl_2$ and $MnCl_2$ for 20-30 minutes at 37° C. APC-anti-Flag antibody (1 mg/ml) and Hoechst (10 mg/ml) were also added 1:750 and 1:5000 to the labeling reaction. Cells were washed three times with PBS and Fluorescence Imaging Media (Life Technologies, Thermo Fisher Scientific, Inc., Waltham, Mass.) was added. Cells were imaged on an EVOS FL-Auto microscope (Life Technologies, Thermo Fisher Scientific, Inc., Waltham, Mass.) using DAPI, RFP and Cy5 fluorescence cubes, and 20× or 40× coverslip-corrected Plan Fluor objectives.

Example 2

Materials

All coding sequences were obtained as codon-optimized synthetic DNA from Life Technologies (Thermo Fisher Scientific, Inc., Waltham, Mass.) or Integrated DNA Technologies, Inc. (Coralville, Iowa). Staple strands for the six-helix bundle were purchased from Life Technologies (Thermo Fisher Scientific, Inc., Waltham, Mass.). All other oligonucleotides were purchased from Integrated DNA Technologies, Inc. (Coralville, Iowa).

Restriction enzymes, T4 ligase, M13mp18 ssDNA, and Hi-Fi DNA Assembly Master Mix were acquired from New England Biolabs, Inc., Ipswich, Mass.). In-Fusion HD Cloning Mix was purchased from Clontech Laboratories, Inc. (Mountain View, Calif.). Salmon sperm DNA was purchased from Life Technologies, Inc. (Thermo Fisher Scientific, Inc., Waltham, Mass.). All common chemicals and media reagents were purchased from Fisher Scientific (Thermo Fisher Scientific, Inc., Waltham, Mass.) unless otherwise specified. All fluorescent imaging reagents were purchased from Life Technologies (Thermo Fisher Scientific, Inc., Waltham, Mass.) unless otherwise specified. Electrophoresis supplies were purchased from Bio-Rad Laboratories, Inc. (Hercules, Calif.) unless otherwise specified.

Buffers

The following buffers were used in protein purification: His6 Lysis buffer (50 mM Tris-HCl, pH 8.0, 350 mM NaCl, 5 mM β-mercaptoethanol, 10 mM imidazole), 6×His Hi-salt wash (50 mM Tris-HCl, pH 8.0, 1 M NaCl, 5 mM β-mercaptoethanol, 10 mM imidazole). Three buffers were used for cell preparation and imaging of intracellular HUH-fusions: Tris-Buffered Saline (TBS, 100 mM Tris-HCl, pH 7.5, 150 mM NaCl), Cytoskeleton Buffer with Sucrose (CBS, 10 mM IVIES, pH 6.1, 138 mM KCl, 3 mM $MgCl_2$, 2 mM EGTA, 0.32 M sucrose), Permeabilization buffer (TBS+0.025% saponin+1% BSA+5 mM MgCl$_2$, 0.5-1 mM MnCl$_2$). DNA origami structures were folded in Tris-EDTA+Mg$^{2+}$ (TEM, 10 mM TrisHCl, pH 8.0, 1 mM EDTA, 10 mM MgCl$_2$).

Protein Expression and Purification

Linear coding DNA was inserted into vector pTD68_6xHis-SUMO at the BamHI and XhoI sites using restriction-based ligation, INFUSION (Clontech Laboratories, Inc., Mountain View, Calif.), or Hi-Fi DNA Assembly. Sequenced constructs were transformed into *Escherichia coli* BL21(DE3) cells and grown in in LB supplemented with 100 µg/mL ampicillin. At OD$_{600}$ 0.8, the cells were induces with 500 µM isopropyl β-D-1-thiogalactopyranoside (IPTG) and allowed to express for three hours at 37° C. or overnight at 18° C. Cells were harvested, the pellet resuspended in 6xHis Lysis buffer, and lysed by sonication. Soluble protein was batch-bound to nickel-NTA agarose (Thermo Fisher Scientific, Inc., Waltham, Mass.) and washed with five column volumes 6xHis Hi-salt wash, then eluted with 6xHis Lysis buffer containing 250 mM imidazole. The purified protein was dialyzed overnight against 50 mM Tris-HCl, pH 8.0, 350 mM NaCl, and 5 mM β-mercaptoethanol or directly concentrated for injection onto size exclusion column. Proteins were further purified by size-exclusion chromatography using an SEC650 column (Bio-Rad Laboratories, Inc., Hercules, Calif.) using 50 mM Tris-HCl, pH 8.0, 200 mM NaCl, and +/−2 mM EDTA. Proteins were concentrated and buffer-exchanged using a VIVASPIN column (GE Healthcare Bio-Sciences, Pittsburgh, Pa.).

To remove the his6-Smt3 fusion tag in the case of TraI36, his-tagged Ulp1 protease was included in the dialysis bag and incubated overnight at 4° C. The protease and Smt3 were then removed by running the solution over nickel-NTA agarose and subsequent size-exclusion chromatography as described above.

SDS-PAGE of Reactions Between HUH-Tags and ssDNA Oligos.

Unless otherwise noted, gel-shift assays were performed in HUH buffer; 50 mM Hepes pH 8, 50 mM NaCl, 1 mM MgCl$_2$ and 1 mM MnCl$_2$, incubated at 37° C. for 15 minutes unless otherwise noted, and quenched with 4× loading buffer. The reactions were analyzed by either electrophoresis on 4-20% polyacrylamide gels stained with Coomassie Blue or Bio-Rad Stain-Free gels. For comparison of covalent adduct formation of SNAP and DCV, 25 pmol of SNAP/DCV proteins were mixed with 100 pmol respective DNA-oligo in SNAP/HUH buffer. 4×SDS loading buffer was added at indicated times to quench. SNAP buffer: 50 mM Hepes pH8, 50 mM NaCl, and 5 mM β-mercaptoethanol. Specificity reactions of HUH-proteins with each target-oligo were performed in HUH buffer with 150 mM NaCl.

Fluorescence De-Quenching Assays

Oligonucleotides were purchased with a 5' quencher and 3' FAM or Cy3 from IDT and dissolved at 100 µM in water. Oligos were diluted to designated concentration (125 mM to 500 nM) in water and 50 µL was added to wells in black 96-well plates. Proteins were dissolved at designated concentration in desired buffer, and 50 µL added to wells containing fluorophore-quencher oligo. Fluorescence of FAM or Cy3 was measured on a fluorescence plate reader (GEMINI, Molecular Devices, LLC, Sunnyvale, Calif.). For experiments using different buffers, each trace was corrected for fluorescence of oligo alone in designated buffer.

Oligonucleotide Labeling

Amino-modified oligonucleotides were obtained from Integrated DNA Technologies, Inc. (Coralville, Iowa) with standard desalting and resuspended in MilliQ water (EMD Millipore, Billerica, Mass.) to 200 µM concentration. N-hydroxy-succinimide (NHS) ester dyes were obtained from Life Technologies, Inc. (Thermo Fisher Scientific, Inc., Waltham, Mass.) and resuspended to 10 mg/mL in anhydrous DMSO. Labeling was performed by mixing 20 µL dye solution, 20 µL DNA, 20 µL 0.5M HEPES, pH 8.5, and 40 µL water and incubating the mixture overnight at room temperature. Excess dye was removed by repeated ethanol precipitation and purification using G-50 spin columns (IBI Scientific, Peosta, Iowa). The SNAP substrate was prepared as above using an amino oligo and the NETS-ester of benzylguanine (New England Biolabs, Inc., Ipswich, Mass.). The reaction was purified on a DNA-Pac column on an NGC purification system (Bio-Rad Laboratories, Inc., Hercules, Calif.) and concentrated using 3 k MWCO centrifugal filters (EMD Millipore, Billerica, Mass.).

Six-Helix Bundle Preparation

The construct was designed using CadNano2 (GitHub, Inc., San Francisco, Calif.). Staple strands were mixed at 10-fold excess with 10 nM m13mp18 scaffold in TEM Buffer and folded by cooling from 80° C. to 60° C. over 80 minutes, then 60° C. to 24° C. over 15 hours. Excess staples were removed by diluting the reaction ten-fold in TEM buffer and concentrating it using 100 k MWCO columns (AMICON, EMD Millipore, Billerica, Mass.) spun at 1,000×g, with two changes of buffer.

DNA Origami Labeling 1 nM six-helix bundle was incubated with 10-fold excess of the selected proteins under standard reaction conditions. The products were analyzed on 2% agarose in 0.5×TBE+11 mM MgCl$_2$ and stained with SYBR Safe (Invitrogen, Thermo Fisher Scientific, Inc., Waltham, Mass.).

Transmission Electron Microscopy

Structures were negative-stained with uranyl formate as described previously [please provide a citation for the "described previously"] and imaged at 88,000× magnification using transmission electron microscopy operating at 60 kv. DNA-protein complexes were immunolabeled using a biotinylated mouse monoclonal anti-6xHis antibody (cat. no. MA121315BTIN) labeled with 20 nm gold-streptavidin (Sigma-Aldrich, St. Louis, Mo.).

Mammalian Vector Construction

Constitutive expression vectors (denoted pcDNA3_Name) were constructed by inserting the coding sequence into the BamHI site of pcDNA3 (Invitrogen, Thermo Fisher Scientific, Inc., Waltham, Mass.) using Hi-Fi DNA Assembly (New England Biolabs, Inc., Ipswich, Mass.). Actin vectors were constructed by inserting the coding sequence of human β-actin into pcDNA3_mTraI36 and pcDNA3_mMobA using BamHI and XhoI, to create a C-terminal in-frame fusion. For cell-surface fusions, existing Flag-Notch1-Gal4 Notch vectors (Gordon et al., *Developmental Cell* 1-9 (2015)) were cut with Kpn1 between the Flag tag and EGF-1 or EGF-24 for truncated receptors, and the codon optimized HUH-tag was inserted by INFUSION (Clontech Laboratories, Inc., Mountain View, Calif.).

Cell Lysate Labeling

HEK293T cells were grown in DMEM/FBS (Corning, Inc. Corning, N.Y.) to 90% confluency in 12-well plates and transfected with 1 µg of vector (pcDNA3) using LIPOFECTAMINE 3000 (Life Technologies, Inc., Thermo Fisher Scientific, Inc., Waltham, Mass.). Transfected cells were grown for 48 hours before being lysed with 300 µL Pierce IP Lysis Buffer (Thermo Scientific, INc., Waltham, Mass.) according to manufacturer's instructions. 10 of cell lysate was incubated at 37° C. for 30 minutes with 1 μL TAMRA-labeled target DNA with or without the addition of 20 mM $MgCl_2$ and 1 mM $MnCl_2$. The reactions were then separated by SDS-PAGE and imaged using a TYPHOON FLA9500 imager (GE Healthcare Bio-Sciences, Pittsburgh, Pa.).

Fixed-Cell Labeling

U2OS cells were grown either on glass coverslips in 6-well dishes or 12-well chambered coverglass (MatTek Corp., Ashland, Mass.) at 37° C. with 5% $CO_2$. At 30-50% confluence, the cells were transfected using LIPO-FECTAMINE 3000 (Life Technologies, Inc., Thermo Fisher Scientific, Inc., Waltham, Mass.). After 24 hours of expression the cells were fixed and permeabilized by the following protocol: 15-minute fixation in 4% paraformaldehyde (Thermo Fisher Scientific, Inc., Waltham, Mass.) in CBS, three two-minutes washes with TBS+0.3 M glycine permeabilized with permeabilization/blocking buffer, 30-minute labeling by addition of 100 nM Alexa 647 oligo to the permeabilization buffer, two three-minute washes with TBS+0.5 M NaCl, a three-minute wash with TBS+two drops of NucBlue Fixed-Cell Stain (Life Technologies, Inc., Thermo Fisher Scientific, Inc., Waltham, Mass.), mounting in SLOWFADE Diamond (Life Technologies, Inc., Thermo Fisher Scientific, Inc., Waltham, Mass.).

Live Cell Surface Labeling

U2OS cells were transiently transfected with full-length or truncated Notch receptors harboring an N-terminal Flag plus mMobA, RepBm, or SNAP fusion tag and intracellular Gal4 fusion for transcriptional assays in 96-well plates using LIPOFECTAMINE 3000 (Life Technologies, Inc., Thermo Fisher Scientific, Inc., Waltham, Mass.). 100 ng of plasmid was used per well. 24-48 hours later, cells were washed twice with PBS, and labeling solution added. Standard labeling solution used a base of standard DMEM, 10% FBS, 1% PenStrep, 1 mM $MnCl_2$, 1 mM $MgCl_2$, 1:20 Salmon Sperm DNA, and 200-250 nM fluorescent oligonucleotide. APC-anti-Flag was added as required at 1:750. Reactions were performed at 37° C. for 20 minutes. Cells were then washed three times with PBS and media was replaced with FLUOROBRITE DMEM media (Life Technologies, Inc., Thermo Fisher Scientific, Inc., Waltham, Mass.) containing FBS+2 μg/mL Hoescht. Luciferase assays were performed by co-transfecting luciferase reporter plasmids, and plating cells in wells coated with 10 μg/ml Jagged1 (R&D Systems, Inc., Minneapolis, Minn.). Cells were lysed and Dual Luciferase Assay (Promega Corp., Madison, Wis.) was performed according to manufacturer's instructions.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

Sequence Listing Free Text

Expression in *E. coli*: General sequence of fusion polypeptide expressed from His6-SUMO-vector, where HUH protein inserts are inserted at the C-terminal of SEQ ID NO:1.

```
                                            (SEQ ID NO: 1)
MRGSHHHHHH MASGSDSEVN QEAKPEVKPE VKPETHINLK

VSDGSSEIFF KIKKTTPLRR LMEAFAKRQG KEMDSLRFLY

DGIRIQADQT PEDLDMEDND IIEAHREQIG
```

HUH protein inserts (metal-coordinating amino acids are underlined, catalytic tyrosine residues is italicized and underlined):

```
PCV2- porcine circovirus 2 (Uniprot Q8BB16)
                                            (SEQ ID NO: 2)
SPSKKNGRSG PQPHKRWVFT LNNPSEDERK KIRDLPISLF

DYFIVGEEGN EEGRTPHLQG FANFVKKQTF NKVKWYLGAR

CHIEKAKGTD QQNKEYCSKE GNLLMEEGAP RSQGQR

GeneA* from PhiX174 (Uniprot P03631) Y131H mutant
                                            (SEQ ID NO: 3)
KSRRGFAIQR LMNAMRQAHA DGWFIVFDTL TLADDRLEAF

YDNPNALRDY FRDIGRMVLA AEGRKANDSH ADCYQYFCVP

EYGTANGRLH FHAVHFMRTL PTGSVDPNFG RRVRNRRQLN

SLQNTWPYGH SMPIAVRYTQ DAFSRSGWLW PVDAKGEPLK

ATSYMAVGFY VAKYVNKKSD MDLAAKGLGA KEWNNSLKTK

LSLLPKKLFR IRMSRNFGMK MLTMTNLSTE CLIQLTKLGY
```

```
DATPFNQILK QNAKREMRLR LGKVTVADVL AAQPVTTNLL

KFMRASIKMI GVSNLQSFIA SMTQKLTLSD ISDESKNYLD

KAGITTACLR IKSKWTAGGK
``` mMobA- minimal catalytic domain of mobilization
protein A from ECOLX plasmid R1162(Uniprot P07112)
(SEQ ID NO: 4)
```
MAIYHLTAKT GSRSGGQSAR AKADYIQREG KYARDMDEVL

HAESGHMPEF VERPADYWDA ADLYERANGR LFKEVEFALP

VELTLDQQKA LASEFAQHLT GAERLPYTLA IHAGGGENPH

CHLMISERIN DGIERPAAQW FKRYNGKTPE KGGAQKTEAL

KPKAWLEQTR EAWADHANRA LERAGH
```

TraI36- IncF plasmid conjugative transfer
DNA-nicking and unwinding protein TraI36
(Uniprot W0FXP9)
(SEQ ID NO: 5)
```
MMSIAQVRSA GSAGNYYTDK DNYYVLGSMG ERWAGRGAEQ

LGLQGSVDKD VFTRLLEGRL PDGADLSRMQ DGSNRHRPGY

DLTFSAPKSV SMMAMLGGDK RLIDAHNQAV DFAVRQVEAL

ASTRVMTDGQ SETVLTGNLV MALFNHDTSR DQEPQLHTHA

VVANVTQHNG EWKTLSSDKV GKTGFIENVY ANQIAFGRLY

REKLKEQVEA LGYETEVVGK HGMWEMPGVP VEAFSGRSQT

IREAVGEDAS LKSRDVAALD TRKSKQHVDP EIKMAEWMQT

LKETGFDIRA YRDAADQRAD LRTLTPGPAS QDGPDVQQAV

TQAIAGLSER
```

RepB- replication associated protein B
from plasmid pMV158 of Streptococcus
agalactiae (Uniprot P13921)
(SEQ ID NO: 6)
```
MAKEKARYFT FLLYPESIPS DWELKLETLG VPMAISPLHD

KDKSSIKGQK YKKAHYHVLY IAKNPVTADS VRKKIKLLLG

EKSLAMVQVV LNVENMYLYL THESKDAIAK KKHVYDKADI

KLINNFDIDR YLE
```

FBNYV- master replication protein from Fava bean
necrotic yellows virus (Uniprot Q9WIJ5)
(SEQ ID NO: 7)
```
MARQVICWCF TLNNPLSPLS LHDSMKYLVY QTEQGEAGNI

HFQGYIEMKK RTSLAGMKKL IPGAHFEKRR GTQGEARAYS

MKEDTRLEGP WEYGEFVP
```

NES- nicking protein from Staphylococcus aureus
plasmid pLW1043 (Uniprot O87361)
(SEQ ID NO: 8)
```
AMYHFQNKFV SKANGQSATA KSAYNSASRI KDFKENEFKD

YSNKQCDYSE ILLPNNADDK FKDREYLWNK VHDVENRKNS

QVAREIIIGL PNEFDPNSNI ELAKEFAESL SNEGMIVDLN

IHKINEENPH AHLLCTLRGL DKNNEFEPKR KGNDYIRDWN

TKEKHNEWRK RWENVQNKHL EKNGFSVRVS ADSYKNQNID

LEPTKKEGWK ARKFEDETG
```

TrwC- conjugative relaxase for E coli plasmid IncW
R388 (Uniprot Q47673)
(SEQ ID NO: 9)
```
MLSHMVLTRQ DIGRAASYYE DGADDYYAKD GDASEWQGKG

AEELGLSGEV DSKRFRELLA GNIGEGHRIM RSATRQDSKE

RIGLDLTFSA PKSVSLQALV AGDAEIIKAH DRAVARTLEQ

AEARAQARQK IQGKTRIETT GNLVIGKFRH ETSRERDPQL

HTHAVILNMT KRSDGQWRAL KNDEIVKATR YLGAVYNAEL

AHELQKLGYQ LRYGKDGNFD LAHIDRQQIE GFSKRTEQIA

EWYAARGLDP NSVSLEQKQA AKVLSRAKKT SVDREALRAE

WQATAKELGI DFS
```

TLYCV- replication associated protein for Tomato
yellow leaf curl virus (Uniprot P27259)
(SEQ ID NO: 10)
```
MPRLFKIYAK NYFLTYPNCS LSKEEALSQL KKLETPTNKK

YIKVCKELHE NGEPHLHVLI QFEGKYQCKN QRFFDLVSPN

RSAHFHPNIQ AAKSSTDVKT YVEKDGNFID FGVSQIDGRS
```

Target DNA sequences (oriT): * denotes predicted nick site:

GeneA:
(SEQ ID NO: 11)
```
TCGACAACTTGA*TATTAATAACACTATAGAC
```

PCV2:
(SEQ ID NO: 12)
```
AAGTATT*ACCAG
```

TraI36:
(SEQ ID NO: 13)
```
TTTGCGTGGGGTGT*GGTGCTTT
``` mMobA:
(SEQ ID NO: 14)
```
CCAGTTTCTCGAAGAGAAACCGGTAAATGCG*CCCT
```

REPB:
(SEQ ID NO: 15)
```
TGCTTCCGTACTACG*ACCCCCA
```

Mammalian constructs (HUH polypeptide fragment is in bold):

Flag-mMobA-Notch1-Gal4
(SEQ ID NO: 16)
```
MPPLLAPLLC LALLPALAAR GSGDYKDDDD KGTGGMAIYH

LTAKTGSRSG GQSARAKADY IQREGKYARD MDEVLHAESG

HMPEFVERPA DYWDAADLYE RANGRLFKEV EFALPVELTL

DQQKALASEF AQHLTGAERL PYTLAIHAGG GENPHCHLMI

SERINDGIER PAAQWFKRYN GKTPEKGGAQ KTEALKPKAW

LEQTREAWAD HANRALERAG HGSGTCSQPG ETCLNGGKCE

AANGTEACVC GGAFVGPRCQ DPNPCLSTPC KNAGTCHVVD

RRGVADYACS CALGFSGPLC LTPLDNACLT NPCRNGGTCD

LLTLTEYKCR CPPGWSGKSC QQADPCASNP CANGGQCLPF

EASYICHCPP SFHGPTCRQD VNECGQKPGL CRHGGTCHNE

VGSYRCVCRA THTGPNCERP YVPCSPSPCQ NGGTCRPTGD

VTHECACLPG FTGQNCEENI DDCPGNNCKN GGACVDGVNT
```

-continued

YNCRCPPEWT GQYCTEDVDE CQLMPNACQN GGTCHNTHGG

YNCVCVNGWT GEDCSENIDD CASAACFHGA TCHDRVASFY

CECPHGRTGL LCHLNDACIS NPCNEGSNCD TNPVNGKAIC

TCPSGYTGPA CSQDVDECSL GANPCEHAGK CINTLGSFEC

QCLQGYTGPR CEIDVNECVS NPCQNDATCL DQIGEFQCIC

MPGYEGVHCE VNTDECASSP CLHNGRCLDK INEFQCECPT

GFTGHLCQYD VDECASTPCK NGAKCLDGPN TYTCVCTEGY

TGTHCEVDID ECDPDPCHYG SCKDGVATFT CLCRPGYTGH

HCETNINECS SQPCRHGGTC QDRDNAYLCF CLKGTTGPNC

EINLDDCASS PCDSGTCLDK IDGYECACEP GYTGSMCNIN

IDECAGNPCH NGGTCEDGIN GFTCRCPEGY HDPTCLSEVN

ECNSNPCVHG ACRDSLNGYK CDCDPGWSGT NCDINNNECE

SNPCVNGGTC KDMTSGYVCT CREGFSGPNC QTNINECASN

PCLNQGTCID DVAGYKCNCL LPYTGATCEV VLAPCAPSPC

RNGGECRQSE DYESFSCVCP TGWQAGQTCE VDINECVLSP

CRHGASCQNT HGGYRCHCQA GYSGRNCETD IDDCRPNPCH

NGGSCTDGIN TAFCDCLPGF RGTFCEEDIN ECASDPCRNG

ANCTDCVDSY TCTCPAGFSG IHCENNTPDC TESSCFNGGT

CVDGINSFTC LCPPGFTGSY CQHDVNECDS QPCLHGGTCQ

DGCGSYRCTC PQGYTGPNCQ NLVHWCDSSP CKNGGKCWQT

HTQYRCECPS GWTGLYCDVP SVSCEVAAQR QGVDVARLCQ

HGGLCVDAGN THHCRCQAGY TGSYCEDLVD ECSPSPCQNG

ATCTDYLGGY SCKCVAGYHG VNCSEEIDEC LSHPCQNGGT

CLDLPNTYKC SCPRGTQGVH CEINVDDCNP PVDPVSRSPK

CFNNGTCVDQ VGGYSCTCPP GFVGERCEGD VNECLSNPCD

ARGTQNCVQR VNDFHCECRA GHTGRRCESV INGCKGKPCK

NGGTCAVASN TARGFICKCP AGFEGATCEN DARTCGSLRC

LNGGTCISGP RSPTCLCLGP FTGPECQFPA SSPCLGGNPC

YNQGTCEPTS ESPFYRCLCP AKFNGLLCHI LDYSFGGGAG

RDIPPPLIEE ACELPECQED AGNKVCSLQC NNHACGWDGG

DCSLNFNDPW KNCTQSLQCW KYFSDGHCDS QCNSAGCLFD

GFDCQRAEGQ CNPLYDQYCK DHFSDGHCDQ GCNSAECEWD

GLDCAEHVPE RLAAGTLVVV VLMPPEQLRN SSFHFLRELS

RVLHTNVVFK RDAHGQQMIF PYYGREEELR KHPIKRAAEG

WAAPDALLGQ VKASLLPGGS EGGRRRRELD PMDVRGSIVY

LEIDNRQCVQ ASSQCFQSAT DVAAFLGALA SLGSLNIPYK

IEAVQSETVE PPPPAQLHFM YVAAAAFVLL FFVGCGVLLS

RKRRRQHGQL WFPEVKLLSS IEQACDICRL KKLKCSKEKP

KCAKCLKNNW ECRYSPKTKR SPLTRAHLTE VESRLERLEQ

LFLLIFPRED LDMILKMDSL QDIKALLTGL FVQDNVNKDA

-continued

VTDRLASVET DMPLTLRQHR ISATSSSEES SNKGQRQLTV

SPHGYLSDVA SPPLLPSPFQ QSPSVPLNHL PGMPDTHLGI

GHLNVAAKPE MAALGGGGRL AFETGPPRLS HLPVASGTST

VLGSSSGGAL NFTVGGSTSL NGQCEWLSRL QSGMVPNQYN

PLRGSVAPGP LSTQAPSLQH GMVGPLHSSL AASALSQMMS

YQGLPSTRLA TQPHLVQTQQ VQPQNLQMQQ QNLQPANIQQ

QQSLQPPPPP PQPHLGVSSA ASGHLGRSFL SGEPSQADVQ

PLGPSSLAVH TILPQESPAL PTSLPSSLVP PVTAAQFLTP

PSQHSYSSPV DNTPSHQLQV PEHPFLTPSP ESPDQWSSSS

PHSNVSDWSE GVSSPPTSMQ SQIARIPEAF K

Flag-TraI36-Notch1-Gal4

(SEQ ID NO: 17)

MPPLLAPLLC LALLPALAAR GSGDYKDDDD KGTGSSGMMS

IAQVRSAGSA GNYYTDKDNY YVLGSMGERW AGRGAEQLGL

QGSVDKDVFT RLLEGRLPDG ADLSRMQDGS NRHRPGYDLT

FSAPKSVSMM AMLGGDKRLI DAHNQAVDFA VRQVEALAST

RVMTDGQSET VITGNLVMAL FNHDTSRDQE PQLHTHAVVA

NVTQHNGEWK TLSSDKVGKT GFIENVYANQ IAFGRLYREK

LKEQVEALGY ETEVVGKHGM WEMPGVPVEA FSGRSQTIRE

AVGEDASLKS RDVAALDTRK SKQHVDPEIK MAEWMQTLKE

TGFDIRAYRD AADQRADLRT LTPGPASQDG PDVQQAVTQA

IAGLSERGTC SQPGETCLNG GKCEAANGTE ACVCGGAFVG

PRCQDPNPCL STPCKNAGTC HVVDRRGVAD YACSCALGFS

GPLCLTPLDN ACLTNPCRNG GTCDLLTLTE YKCRCPPGWS

GKSCQQADPC ASNPCANGGQ CLPFEASYIC HCPPSFHGPT

CRQDVNECGQ KPGLCRHGGT CHNEVGSYRC VCRATHTGPN

CERPYVPCSP SPCQNGGTCR PTGDVTHECA CLPGFTGQNC

EENIDDCPGN NCKNGGACVD GVNTYNCRCP PEWTGQYCTE

DVDECQLMPN ACQNGGTCHN THGGYNCVCV NGWTGEDCSE

NIDDCASAAC FHGATCHDRV ASFYCECPHG RTGLLCHLND

ACISNPCNEG SNCDTNPVNG KAICTCPSGY TGPACSQDVD

ECSLGANPCE HAGKCINTLG SFECQCLQGY TGPRCEIDVN

ECVSNPCQND ATCLDQIGEF QCICMPGYEG VHCEVNTDEC

ASSPCLHNGR CLDKINEFQC ECPTGFTGHL CQYDVDECAS

TPCKNGAKCL DGPNTYTCVC TEGYTGTHCE VDIDECDPDP

CHYGSCKDGV ATFTCLCRPG YTGHHCETNI NECSSQPCRH

GGTCQDRDNA YLCFCLKGTT GPNCEINLDD CASSPCDSGT

CLDKIDGYEC ACEPGYTGSM CNINIDECAG NPCHNGGTCE

DGINGFTCRC PEGYHDPTCL SEVNECNSNP CVHGACRDSL

NGYKCDCDPG WSGTNCDINN NECESNPCVN GGTCKDMTSG

YVCTCREGFS GPNCQTNINE CASNPCLNQG TCIDDVAGYK

CNCLLPYTGA TCEVVLAPCA PSPCRNGGEC RQSEDYESFS

-continued

CVCPTGWQAG QTCEVDINEC VLSPCRHGAS CQNTHGGYRC

HCQAGYSGRN CETDIDDCRP NPCHNGGSCT DGINTAFCDC

LPGFRGTFCE EDINECASDP CRNGANCTDC VDSYTCTCPA

GFSGIHCENN TPDCTESSCF NGGTCVDGIN SFTCLCPPGF

TGSYCQHDVN ECDSQPCLHG GTCQDGCGSY RCTCPQGYTG

PNCQNLVHWC DSSPCKNGGK CWQTHTQYRC ECPSGWTGLY

CDVPSVSCEV AAQRQGVDVA RLCQHGGLCV DAGNTHHCRC

QAGYTGSYCE DLVDECSPSP CQNGATCTDY LGGYSCKCVA

GYHGVNCSEE IDECLSHPCQ NGGTCLDLPN TYKCSCPRGT

QGVHCEINVD DCNPPVDPVS RSPKCFNNGT CVDQVGGYSC

TCPPGFVGER CEGDVNECLS NPCDARGTQN CVQRVNDFHC

ECRAGHTGRR CESVINGCKG KPCKNGGTCA VASNTARGFI

CKCPAGFEGA TCENDARTCG SLRCLNGGTC ISGPRSPTCL

CLGPFTGPEC QFPASSPCLG GNPCYNQGTC EPTSESPFYR

CLCPAKFNGL LCHILDYSFG GGAGRDIPPP LIEEACELPE

CQEDAGNKVC SLQCNNHACG WDGGDCSLNF NDPWKNCTQS

LQCWKYFSDG HCDSQCNSAG CLFDGFDCQR AEGQCNPLYD

QYCKDHFSDG HCDQGCNSAE CEWDGLDCAE HVPERLAAGT

LVVVVLMPPE QLRNSSFHFL RELSRVLHTN VVFKRDAHGQ

QMIFPYYGRE EELRKHPIKR AAEGWAAPDA LLGQVKASLL

PGGSEGGRRR RELDPMDVRG SIVYLEIDNR QCVQASSQCF

QSATDVAAFL GALASLGSLN IPYKIEAVQS ETVEPPPPAQ

LHFMYVAAAA FVLLFFVGCG VLLSRKRRRQ HGQLWFPEVK

LLSSIEQACD ICRLKKLKCS KEKPKCAKCL KNNWECRYSP

KTKRSPLTRA HLTEVESRLE RLEQLFLLIF PREDLDMILK

MDSLQDIKAL LTGLFVQDNV NKDAVTDRLA SVETDMPLTL

-continued

RQHRISATSS SEESSNKGQR QLTVSPHGYL SDVASPPLLP

SPFQQSPSVP LNHLPGMPDT HLGIGHLNVA AKPEMAALGG

GGRLAFETGP PRLSHLPVAS GTSTVLGSSS GGALNFTVGG

STSLNGQCEW LSRLQSGMVP NQYNPLRGSV APGPLSTQAP

SLQHGMVGPL HSSLAASALS QMMSYQGLPS TRLATQPHLV

QTQQVQPQNL QMQQQNLQPA NIQQQQSLQP PPPPPQPHLG

VSSAASGHLG RSFLSGEPSQ ADVQPLGPSS LAVHTILPQE

SPALPTSLPS SLVPPVTAAQ FLTPPSQHSY SSPVDNTPSH

QLQVPEHPFL TPSPESPDQW SSSSPHSNVS DWSEGVSSPP

TSMQSQIARI PEAFK

SEQ ID NO: 18 ccagtttctcgaagagaaaccggtaagtgca-ccctccc

SEQ ID NO: 19 acgcgaacggaacgttcgcataagtgcgcccttacgggatttaac

HUH protein inserts (metal-coordinating amino acids are underlined, catalytic tyrosine residues is italicized and underlined):

RepBm- Plasmid replication protein RepB from *Streptococcus pnemoniae* (Uniprot A0A0T8A2Q2)

SEQ ID NO: 20

MSEKKEIVKG RDWTFLVYPE SAPENWRTIL DETFMRWVES

PLHDKDVNAD GEIKKPHWHI LLSSDGPITQ TAVQKIIGPL

NCPNAQKVGS AKGLVR*Y*MVH LDNPEKYQYS LDEIVGHNGA

DVASYFELTA

DCV-duck circovirus (Uniprot A7LI84)

SEQ ID NO: 21

MAKSGNYSYK RWVFTINNPT FEDYVHVLEF CTLDNCKFAI

VGEEKGANGT PHLQGFLNLR SNARAAALEE SLGGRAWLSR

ARGSDEDNEE *Y*CAKESTYLR VGEPVSKGRS S

What is claimed is:

1. A fusion polypeptide comprising:
    at least a portion of a polypeptide of interest; and
    at least a functional portion of an HUH polypeptide Rep/relaxase domain, wherein the HUH polypeptide Rep/relaxase domain comprises:
        a catalytic tyrosine residue;
        at least one and no more than two metal-coordinating histidine residues; and
        endonuclease nicking activity.

2. The fusion polypeptide of claim 1 further comprising a detectable label.

3. A complex comprising:
    an oligonucleotide; and
    a fusion polypeptide that specifically binds to the oligonucleotide, the fusion polypeptide comprising:
        at least a portion of a polypeptide of interest; and
        at least a functional portion of an HUH polypeptide Rep/relaxase domain, wherein the HUH polypeptide Rep/relaxase domain comprises:
            a catalytic tyrosine residue;
            at least one and no more than two metal-coordinating histidine residues; and
            endonuclease nicking activity.

4. The complex of claim 3 wherein the oligonucleotide comprises DNA.

5. The complex of claim 4 wherein the DNA comprises DNA origami.

6. The complex of claim 3 wherein the oligonucleotide comprises RNA.

7. The complex of claim 6 wherein the RNA comprises RNA origami.

8. A composition comprising:
    an oligonucleotide; and
    a fusion polypeptide that specifically binds to the oligonucleotide, the fusion polypeptide comprising:

at least a portion of a polypeptide of interest; and at least a functional portion of an HUH polypeptide Rep/relaxase domain, wherein the HUH polypeptide Rep/relaxase domain comprises:

a catalytic tyrosine residue;

at least one and no more than two metal-coordinating histidine residues; and endonuclease nicking activity.

9. The composition of claim 8 further comprising:

a second oligonucleotide; and a second fusion polypeptide that specifically binds to the second oligonucleotide, the second fusion polypeptide comprising:

at least a portion of a second polypeptide of interest; and at least a functional portion of a second HUH polypeptide Rep/relaxase domain, wherein the second HUH polypeptide Rep/relaxase domain comprises:

a catalytic tyrosine residue;

at least one and no more than two metal-coordinating histidine residues; and endonuclease nicking activity.

* * * * *